US009220258B2

(12) United States Patent
Cook et al.

(10) Patent No.: US 9,220,258 B2
(45) Date of Patent: Dec. 29, 2015

(54) TISSUE PRESERVATION SYSTEM

(75) Inventors: James L. Cook, Columbia, MO (US); Clark T. Hung, Ardsley, NY (US); Eric Lima, New York, NY (US); Aaron Stoker, Columbia, MO (US)

(73) Assignees: The Curators of the University of Missouri, Columbia, MO (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/349,534

(22) Filed: Jan. 12, 2012

(65) Prior Publication Data

US 2012/0177615 A1 Jul. 12, 2012

Related U.S. Application Data

(60) Provisional application No. 61/461,049, filed on Jan. 12, 2011.

(51) Int. Cl.
*C12N 5/00* (2006.01)
*A01N 1/02* (2006.01)
(52) U.S. Cl.
CPC .............. *A01N 1/0263* (2013.01); *A01N 1/021* (2013.01); *A01N 1/0284* (2013.01)
(58) Field of Classification Search
CPC ... A01N 1/021; A01N 1/0215; A01N 1/0231; A01N 1/02; A01N 1/0242
See application file for complete search history.

(56) References Cited

U.S. PATENT DOCUMENTS

| 4,695,536 A | 9/1987 | Lindstrom et al. | |
|---|---|---|---|
| 2008/0113426 A1* | 5/2008 | Smith et al. | 435/286.5 |
| 2009/0076624 A1 | 3/2009 | Rahaman et al. | |
| 2010/0319805 A1 | 12/2010 | Klein | |

FOREIGN PATENT DOCUMENTS

| WO | WO 2008/131973 | 11/2008 |
|---|---|---|
| WO | WO 2010/036726 | 4/2010 |
| WO | WO 2010/049181 | 5/2010 |

OTHER PUBLICATIONS

Feng S., MiniReview—"Donor Intervention and Organ Preservation: Where Is the Science and What Are the Obstacles?", American Journal of Transplantation, 2010 vol. 10, pp. 1155-1162.*
Yang Y. et al., Keeping Donor Hearts in Completely Beating Status With Normothermic Blood Perfusion for Transplants, Ann. Thorac. Surg., 2013 Article in Press, pp. 1-7.*
King Jr. J.H. et al., "The Prolonged Storage of Donor Corneas by Glycerine Dehydration", Th. Am . Ophth. Soc., 1984, Vol. LXXXII, pp. 106-110.*
Tamaki K. et al., K-Sol corneal preservation at room temperature, British Journal of Ophthalmology, 1988, vol. 72, pp. 370-376.*
Voss J. R. et al., Effects of thermal energy on chondrocyte viability, Am. J. Vet. Res., 2006, vol. 67, pp. 1708-1712.*
Bian et al., "Effects of dexamethasone on the functional properties of cartilage explants during long-term culture," *Am J Sports Med*, 38(1):78-85, 2010.
Bian et al., "Efficacy of serum-free medium and dynamic loading in maintenance of long-term cultures of cartilage explants," *Trans Orthop Res Soc*, 32:569, Poster #0569, presented to the Orthopaedic Research Society Annual Meeting, San Diego, CA, 2007.
Bian et al, "Mechanical and biochemical characterization of cartilage explants in serum-free culture," *J Biomechanics*, 41:1153-1159, 2008.
Bian et al., "Effects of dexamethasone on the functional properties of cartilage explants during long-term culture," paper No. 329, presented to the Orthopaedic Research Society 2009 Annual Meeting, 2009.
Bian et al., "Long-term preservation of chondral and osteochondral explants using tissue culture," poster presentation, poster No. 1058, presented to the Orthopaedic Research Society 2008 Annual Meeting, 2008.
Bugbee, MD., "Fresh osteochondral allografts," *J Knee Surg*, 15(3):191-195, 2002.
Byers, et al., "Transient TGF-83 exposure and constant dexamethasone treatment synergistically enhance maturation and functional properties of chondrocyte-laden hydrogels," poster presentation, poster No. 0794, presented to the Orthopaedic Research Society 2006 Annual Meeting, 2006.
Diresta et al., "Bisphosphonate delivery to tubular bone allografts," *Clinical Orthopaedics and Related Research*, 466(8):1871-1879, 2008.
Garrity et al., "Improved Osteochondral allograft preservation using serum-free media at body temperature," *Am J Sports Med*, 40:2542-2548, 2012.
Hung et al., "Tissue age-dependent dexamethasone modulation of cartilage properties in culture," e-Poster presentation, International Cartilage Repair Society, 16 pages, 2009.
Jafari et al., "Dexamethasone attenuation of cytokine-mediated articular cartilage degradation in experimental lapine Haemophilus arthritis," *J Infect Dis*, 168(5):1186-93, 1993.
Jeong et al., "Repair of osteochondral defects with a construct of mesenchymal stem cells and a polydioxanone/poly(vinyl alcohol) scaffold," *Biotechnol Appl Biochem*, 49(Pt 2):155-164, 2008.
Lima et al., "Differences in interleukin-1 response between engineered and native cartilage," *Tissue Eng Part A*, 14(10):1721-1731, 2008.
Martinovic et al., "Requirement of a bone morphogenetic protein for the maintenance and stimulation of osteoblast differentiation," *Arch Histol Cytol*, 69(1):23-36, 2006.

(Continued)

*Primary Examiner* — Satyendra K Singh
(74) *Attorney, Agent, or Firm* — Dentons US LLP

(57) ABSTRACT

The present invention provides a method and apparatus for tissue, such as an allograft, storage and preservation for extended periods of time at room temperature in a sterile tissue culture chamber. The invention further provides a process for maintaining the sterility of tissue using the apparatus as described.

22 Claims, 10 Drawing Sheets

(56) References Cited

OTHER PUBLICATIONS

Morin et al., "Induction of stromelysin gene expression by tumor necrosis factor alpha is inhibited by dexamethasone, salicylatem and N-acetylcysteine in synovial fibroblasts," *J Pharmacol Exp Ther*, 289(3):1634-40, 1999.

Moroni et al., "Regenerating articular tissue by converging technologies," *PLoS ONE*, 3(8):1-10, 2008.

Perrot et al., "A new nondestructive cytometric assay based on resazurin metabolism and an organ culture model for the assessment of corneal viability," *Cytometry*, 55A(1); 7-14, Aug. 18, 2003.

Stoker et al., "Analysis and comparison of osteochondral allograft metabolism using various preservation protocols," University of Missouri, Columbia, MO., Poster No. 1450, presented to the Orthopaedic Research Society 2011 Annual Meeting, Long Beach, CA, 2011.

Stoker et al., "Analysis of Osteochondral Allograft Metabolism Using Various Preservation Protocols at 25° C.," Poster #1744, presented to the Orthopaedic Research Society 2012 Annual Meeting, Long Beach, CA, Feb. 4-7, 2012.

Stoker et al., "Assessment of Potential Biomarkers for the Evaluation of Osteochondral Allograft Viability During Preservation," University of Missouri, Columbia, MO., presented to the Orthopaedic Research Society 2011 Annual Meeting, Long Beach, CA, 2011.

Stoker et al., "Improved preservation of fresh osteochondral allografts for clinical use." J Knee Surg, 25(2):117-25, 2012.

Stoker et al., "Optimization of osteochondral allograft preservation to extend the usable life span of harvested tissue," University of Missouri, Columbia, MO., presented to the Orthopaedic Research Society 2011 Annual Meeting, Long Beach, CA, 2011.

ISA; Invitation to Pay Additional Fees and, where applicable, protest fee; regarding International Application No. PCT/US2012/021134, dated May 23, 2012.

International Search Report for PCT/US2012/021134, dated Oct. 11, 2012.

* cited by examiner

TISSUE PRESERVATION SYSTEM

CROSS REFERENCE TO RELATED APPLICATIONS

This application claims the priority of U.S. Provisional Application No. 61/461,049, filed on Jan. 12, 2011, the entire disclosure of which is incorporated herein by reference.

FIELD OF THE INVENTION

The invention relates to the field of tissue, such as an allograft, storage and more specifically to the field of long-term tissue storage and preservation.

BACKGROUND OF THE INVENTION

Allograft or other tissue samples are used to treat many diseases and/or defects. These grafts are procured from organ donors and must be stored to allow for viral and bacterial testing for safety prior to shipping to surgical centers for implantation into patients. Based on studies looking at viability of the cells in the grafts, recommendations have been given for implanting tissues as soon after harvest as possible in order to maximize success. Safety testing takes a minimum of 7 days and more often 10-14 days for final clearance. Storage of tissue, such as allograft tissue, for transplantation or other scientific or medical purposes allows time for medical testing, recipient patient preparation, or to preserve tissues for other purposes. Storage conditions for allograft or other tissue samples may influence tissue viability, integrity, and/or sterility.

SUMMARY OF THE INVENTION

Briefly described, embodiments of this disclosure provide a process and apparatus for tissue preservation. In one aspect, the invention provides a process for tissue preservation by storing the tissue at room temperature in a container with culture media for from about 7 to about 70 days before implantation into a patient. In one embodiment, the tissue is tested for viability at least once prior to implantation in a patient. In another embodiment, viability testing is performed by assaying media that is withdrawn from the container. In another embodiment, cell viability is determined by adding a resazurin solution to the media and determining the fluorescence level, wherein increased fluorescence indicates higher cell viability.

In another embodiment, the tissue is stored in the container for from 29 to about 70 days. In other embodiments, the media is changed at least once or about once every two weeks during storage. In another embodiment, at least about 70% of tissue preserved by this method remains viable after 45 days of storage.

One aspect of the invention provides media used for storage of tissue that is serum-free and can contain Dulbecco's Modified Eagle Medium (DMEM), high or low concentrations of glucose, antibiotic compounds (i.e., penicillin and/or streptomycin), antimycotic compounds (i.e., Fungizone), dexamethasone, ascorbate 2-phosphate, L-proline, sodium pyruvate, TGF-β3, and insulin, transferrin, and selenous acid, among other chemicals or compounds.

In another aspect of the invention, the media is serum-free. In an embodiment, the media contains an effective amount of dexamethasone. In another embodiment, the tissue is a section of spine, scapula, humerus, radius, ulna, pelvis, femur, tibia, patella, talus, phalanges or temporomandibular joint tissue. Other embodiments of this invention provide lavage of the tissue in an isotonic solution prior to storing, and implanting the tissue into a patient after storage.

Another aspect of the present invention provides a process for storage of tissue in a tissue preservation chamber containing a base, lid, media inlet, and media outlet, wherein the media inlet is coupled to at least a first filter for maintaining a sterile environment inside the chamber, the base is configured to contain tissue and media, the outlet extending into the chamber permits removal of media, a one-way valve as the media outlet for removing media from the chamber, and wherein the base is capable of receiving the lid to form a barrier to contaminants. In embodiments of this invention, a gas exchange port is coupled to at least a first filter, and the lid contains the media inlet, media outlet, and gas exchange port. In another embodiments, the tissue is stored in the chamber for from about 29 days to about 60 days.

Another aspect of the present disclosure provides a tissue preservation chamber, including a base, lid, media inlet, and media outlet, wherein the media inlet is coupled to at least a first filter for maintaining a sterile environment inside the chamber, the base is configured to contain cartilage tissue and media, the outlet extends into the chamber to permit removal of media, the media outlet is a one-way valve for exit of media from the chamber, and the base is capable of receiving the lid to form a barrier to contaminants. In other embodiments, a gas exchange port is coupled to at least a first filter, the lid contains the media inlet, media outlet and gas exchange port, and the lid is a filter than extends across the media inlet and gas exchange port. In one embodiment, the filter is a basket adapted to be received by the lid to form a recess for sterile filter paper, the recess being in fluid and gas communication with the media inlet and gas exchange port. In another embodiment, the media inlet and gas exchange port are coupled to different filters for maintaining a sterile environment within the chamber. In another embodiment, the media inlet and gas exchange port are coupled to the same filter to maintain a sterile environment within the chamber. In other embodiments, the media inlet and outlet serve as adaptors for receiving a hose. In another embodiment, the base and lid are configured to form a rim for sealing with tamper-evident tape when in contact.

One exemplary method of tissue storage at room temperature in a chamber with culture media before implantation includes: placing the tissue in a chamber base, the chamber base configured to maintain the tissue and tissue preservation media, and forming a tissue preservation chamber by covering the chamber base with a lid to form a barrier to contaminants, and wherein the lid contains at least one filter, a media inlet coupled to at least one filter for maintaining a sterile environment inside the chamber, and a media outlet, the media outlet including a media outlet conduit that extends into the chamber to permit removal of media and reentry of media exiting the chamber. In an embodiment, the chamber also has a gas exchange port coupled to at least one filter. In another embodiment, the lid comprises the media inlet, media outlet, and gas exchange port.

An aspect of the present invention provides addition of media to the chamber through the media inlet and at least one filter. One embodiment provides storage of the tissue in the chamber for from 29 days to about 70 days. Other embodiments provide removal of the media from the chamber through the media outlet. A further embodiment provides simultaneous addition of media to the chamber by forcing through the media inlet and at least one filter, along with removal of media from the chamber through the media outlet. Another embodiment of the present invention provides applying tamper evident tape to an interface between the chamber base and the lid in order to maintain sterility of the tissue.

The foregoing and other aspects of the invention will become more apparent from the following detailed description.

DETAILED DESCRIPTION

Figure 1:
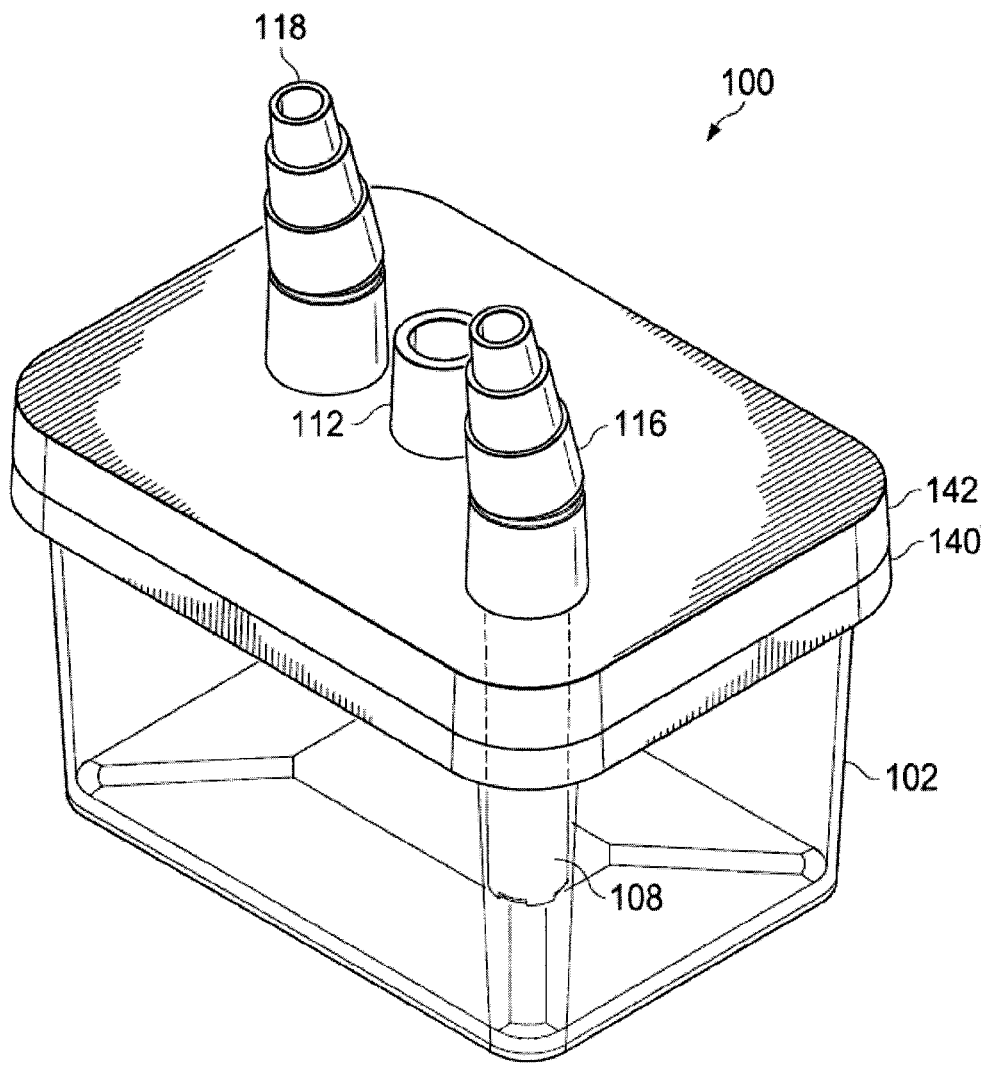
FIG. 1 shows a perspective view of a tissue preservation chamber according to an illustrative embodiment.

The following definitions and methods are provided to better define the present invention and to guide those of ordinary skill in the art in the practice of the present invention. Unless otherwise noted, terms are to be understood according to conventional usage by those of ordinary skill in the relevant art.

The present disclosure provides a process and apparatus for tissue preservation. The process includes, in one embodiment, removing viable tissue, such as allograft tissue, from a donor, testing of the tissue for infectious diseases and/or mechanical and/or biochemical activity for viability, placement of the viable tissue into a sterile tissue culture preservation chamber as described herein with a culture medium capable of maintaining the viability and sterility of the tissue, and storing the tissue for extended periods of time prior to implantation into a recipient. As used herein, the term "allograft" refers to a tissue graft from a donor of the same species as the recipient but not genetically identical. In an embodiment, at least about 90% of tissue or allografts preserved by the process described herein remain viable after 45 days of storage. In another embodiment, the tissue is lavaged in isotonic solution prior to storing. In still another embodiment, the tissue is allograft tissue.

Allograft tissue can be removed from a donor by techniques known in the art. For instance, general aseptic surgical methods or other physical intervention of an allograft may include but are not limited to excision, resection, amputation, transplantation, microsurgery, general surgery, laser surgery, robotic surgery, or autopsy, among others.

Tissue or allograft sources may be cells, tissues, or organs from all types of organisms, including, but not limited to human, porcine, ovine, bovine, canine, equine, and others. In one embodiment, the source of the tissue or allograft is human. Potential allograft sources may include, but are not limited to, tissues of the eye, brain, heart, kidney, liver, intestine, bone, cartilage, skin, lung, thyroid, stomach, ligaments, tendons, or any other tissue and/or cell source that may require transplantation. In one embodiment of the invention, the allograft may comprise bone and/or cartilage and/or meniscus tissue of the spine, scapula, humerus, radius, ulna, pelvis, femur, tibia, fibula, patella, talus, phalanges, or temporomandibular joint. In another embodiment, the allograft may be osteochondral tissue. Although the description herein may refer to allograft tissue, one of skill in the art appreciates that other tissues find use in the method.

Once removed from the donor, the allograft is stored within the sterile tissue culture chamber including, but not limited to, the chamber described herein, for an extended period of time. In one embodiment, the allograft is stored at room temperature in culture media. In specific embodiments, the room temperature is between about 19° C. and 27° C., including about 19° C., 20° C., 21° C., 22° C., 23° C., 24° C., 25° C., 26° C., or about 26° C. In another embodiment, the allograft is stored at a temperature that is not less than about 12° C. and not more than about 30° C.

As used herein, the term "culture media" refers to liquid, semi-solid, or solid media used to support tissue growth and/or preservation and/or development in a non-native environment. Further, by culture media is meant a sterile solution that is capable of stabilizing and preserving the tissue in order to maintain its biological activity and sterility. Suitable tissue culture media are known to one of skill in the art, as discussed in detail subsequently. The media components can be obtained from suppliers other than those identified herein and can be optimized for use by those of skill in the art according to their requirements. Culture media components are well known to one of skill in the art and concentrations and/or components may be altered as desired or needed. In one embodiment, culture media may contain Dulbecco's Modified Eagle Medium (DMEM), glucose, antibiotic compounds, antimycotic compounds, dexamethasome, ascorbate 2-phosphate, L-proline, sodium pyruvate, TGF-β3, insulin, transferrin, and selenous acid, among other chemicals or compounds. In particular, antibiotic compounds may include, but are not limited to penicillin, streptomycin, chloramphenicol, gentamycin, and the like. Antimycotic compounds may include, but are not limited to Fungizone. In an embodiment, the culture media lacks serum. The media-to-tissue ratio within the sterile tissue culture chamber may be 10-50:1 per volume.

An unexpected benefit of the present procedure is that tissue samples can be maintained viable and sterile for an extended period of time relative to methods of the prior art. For instance, typically in the prior art, upon removal of an allograft from a donor, the tissue was stored on ice or at around 4° C. Tissues prepared according to this method tended to remain suitably viable for around 21-28 days. However, the procedure described herein provides for a surprising and unexpected increase in viability of allograft tissue. Tissues prepared and stored according to the procedure described herein remain viable for an extended period of time relative to storage at 4° C. By an extended period is meant at least between about 7-100 days, at least between about 20-80 days, or at least between about 29-70, 40-70, 50-70 or 60-70 days. In one embodiment an extended period is meant up to at least around 70 days.

It has been found that long-term storage of tissue may be facilitated by replacement of old culture medium with fresh, sterile medium. However, prior to the present disclosure, a system that allowed for media exchange in an otherwise non-sterile environment was not available. The present disclosure provides a system and device that allows for just this. Advantageously, the present procedures and device provide for sterile media exchange in an otherwise non-sterile environment. Thus, media can be conveniently changed as necessary. In one embodiment, the media is changed at least once, twice, or three times during storage. The media may be changed without removing a lid from the storage container, or otherwise opening the container. The media may be changed, in specific embodiments, about once every other day, at least once a week, at least once every two weeks, or at least about once a month during storage. In one embodiment, media is aspirated from the sterile chamber through a media outlet, and replaced by adding fresh media through a media inlet, as described in more detail below with regard to FIG. 9. In one embodiment, a filter is placed between the lid and base chamber and media flows through the filter into the chamber. Therefore, the media remains sterile. In addition, the filter enables exchange of $CO_2$ and $O_2$ between the chamber and the surrounding air while maintaining sterility inside the chamber.

Prior to storage according to the present disclosure, testing of allograft tissue encompassed up to or greater than 7 days and required direct contact with the allograft. Such methods increased the likelihood of allograft contamination. The present disclosure provides a convenient and easy method of testing for viability and/or contamination, by simply extracting the culture medium from the culture chamber through the media outlet, which does not compromise sterility of the tissue. The extended storage period allows for examination or testing of the allograft and/or culture media for a number of factors, such as viability, blood type compatibility, HLA typing, genotyping, SNP detection, and/or infection with diseases. Compounds that may be detected or tested may be obtained from culture media withdrawn from the sterile tested such as, but not limited to, bacterial or virus infections, nitric oxide, prostaglandin $E_2$, matrix metalloproteinase (MMP)-2, MMP-3, MMP-9, and MMP-13, vascular endothelial growth factor (VEGF), interleukin (IL)-2, IL-4, IL-6, IL-7, IL-8, IL-10, IL-15, and IL-18, granulocyte macrophage colony-stimulating factor (GM-CSF), Interferon gamma-induced protein (IP)-10, IFNγ, keratinocyte chemoattractant (KC), MCP-1, and TNFα. Tissue may be tested using methods known in the art, such as by diagnostic PCR or with antibodies against biomarkers such as, but not limited to, those described above. The viability of the OCA may also be monitored during storage by adding a resazurin solution to the media at a final concentration of about 10 μg/ml and incubated at room temperature for 18-24 hours. During the incubation, resazurin is converted to resorufin by viable cells in the OCA. A 200-μl sample of the media is taken and the fluorescence level is determined using a fluorescence reader (540-570 nm excitation, 580-610 nm emission). Increased fluorescence is indicative of higher cell viability. Higher viability samples typically have a fluorescence reading of ~800-1200 units using a Synergy HT set at a sensitivity of 25 on the reader.

In view of the above, the process provides for preservation of at least 70% of the allograft tissue chondrocytes after storage at room temperature for 45 days. In an embodiment, at least 60% or 70%, up to at least around 99%, including 60%, 65%, 70%, 75%, 80%, 85%, 90%, or 95% or greater of the tissue is preserved when stored for 45 days, 60 days, or 70 days.

In one embodiment, the process includes storing the tissue in a tissue preservation chamber. In another embodiment, the process further includes implanting the tissue in a subject in need thereof following said storing.

Figure 2A:
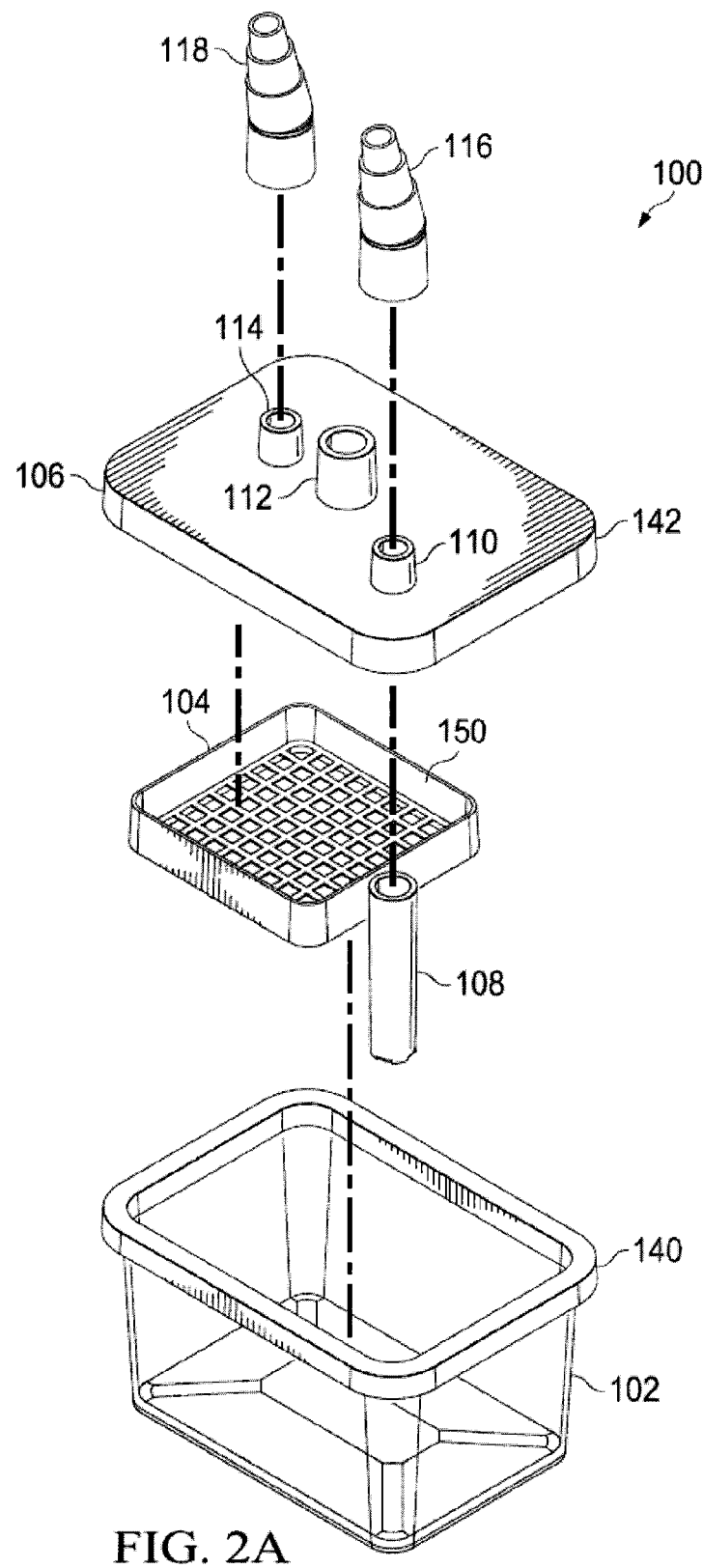
FIG. 2A shows an exploded perspective view illustrating the upper surfaces of the components of the tissue preservation chamber of FIG. 1.
Figure 2B:
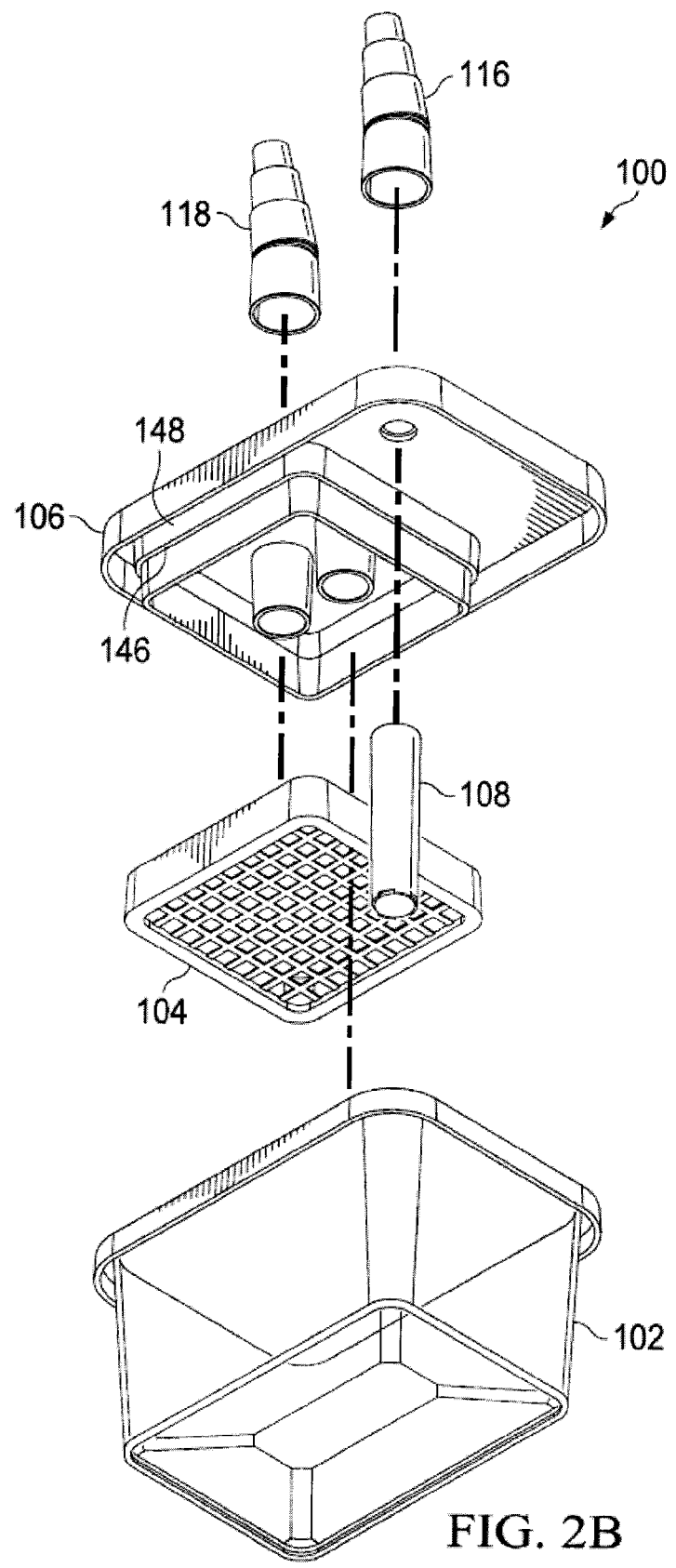
FIG. 2B shows an exploded perspective view illustrating the lower surfaces of the components of the tissue preservation chamber of FIG. 1.

An illustrative embodiment of a tissue preservation chamber 100 is shown in FIGS. 1, 2A, and 2B. The tissue preservation chamber 100 includes a base 102 that may be formed from any suitable material for storing tissue, e.g., an allograft. The tissue preservation chamber 100 also includes a lid 106 that forms a sealed enclosure when applied to the base. To form the sealed enclosure, the base 102 may have a first sealing surface 140 and the lid 106 may include second sealing surface 142 that abut one another when the lid 106 is applied to the base 102. In the illustrative embodiment of FIG. 1, the lid 106 is sized and configured to be installed to the base 102 such that the first sealing surface 140 and second sealing surface 142 are adjacent and coplanar about the periphery of the tissue preservation canister 100. In such an embodiment, a sterile environment may be ensured by applying a tape about the common surface formed at the interface of the lid 106 and base 102. In an embodiment, the lid 106 may be formed with a mating feature, such as a lip on the underside of the lid 106 that forms an interference fit with the interior surface of the base 102. In the illustrative embodiment of FIG. 1, the lid 106 and base 102 have a rectangular shape, though it is noted that the tissue preservation chamber may be of any suitable size and shape.

In an illustrative embodiment, the lid 106 includes features to facilitate the controlled ingress and egress of gas and liquids to and from the tissue preservation chamber 100. These features include a media outlet 110, media inlet 114, and gas exchange port 112. In an embodiment, the lid 106 also includes a filter basket mount 146 that may be used to attach a filter basket 104. The filter basket mount 146 of FIG. 2B is a molded portion of the lid 106 that includes an external surface 148 that mates with a complimentary internal surface 150 of the filter basket 104. In an embodiment, the complimentary surfaces 148, 150 are tapered surfaces. The filter basket 104 and base 102 may also include complementary geometrical features to locate the filter basket 104 to securely hold a filter within the assembled tissue preservation chamber 100. In such an embodiment, the filter basket 104 may be mounted to the base 102 rather than the lid 106. In some embodiments, an adhesive may be used to hold the filter basket in place. As shown in FIG. 2B, the filter basket 104 includes a grated surface to support a filter without obstructing fluid flow between the tissue preservation chamber 100 and the media inlet 114 or gas exchange port 112. The filter basket 104 of FIG. 2B is shown as having a single grated surface to support a single filter. Yet in some embodiments, the tissue preservation chamber 100 may include a filter basket 104 capable of holding multiple filters, or multiple filter baskets to facilitate the use of separate filters for filtering flow through the media inlet 114 and gas exchange port 114.

The top surface of the lid 106 includes protrusions that form the media inlet 114, the gas exchange port 112, and media outlet 110. The media inlet 114 may also form a similar protrusion that extends from the inner surface of the lid 106, and is located inside of the filter basket mount 146 so that fluid entering the tissue preservation chamber 100 via the media inlet 112 is routed through the filter basket 104. The gas exchange port 112 may also form a similar protrusion that extends from the inner surface of the lid 106, and is located inside of the filter basket mount 146 so that fluid entering the tissue preservation chamber 100 via the gas exchange port 112 is forced through the filter basket 104. The protrusions that form the media inlet 114, gas exchange port 112, and media outlet 110 shown in FIGS. 2A and 2B comprise tapered annular members that are suitable for coupling to, e.g., a tubing adapter. Nonetheless, the media inlet 114, gas exchange port 112, and media outlet 110 may have any suitable size and shape to facilitate fluid flow to and from the tissue preservation chamber 100. For example, in an embodiment, the portions of the lid 106 that protrude from the top surface of the lid 106 to form the media inlet 114 and media outlet 110 include a tapered surface to facilitate coupling to tubing adapters 118 and 116, respectively. Similarly, in an illustrative embodiment, the media outlet 110 is fluidly coupled to a media outlet conduit 108 that extends into the tissue preservation chamber 100 to facilitate the removal of fluid from the base of the media outlet conduit 108.

The tissue preservation chamber 100 illustrated in the Figures is operable to store living tissue. In the illustrative embodiments, the media outlet 110 and media inlet 114 facilitate the addition and removal of liquid, e.g., tissue culture media, to and from the tissue preservation chamber 100 while preserving a sealed, sterile environment within the tissue preservation chamber 100. Thus, once made, the tissue preservation chamber 100 described above finds use in a method of allograft preservation in which a tissue sample or allograft is stored in the tissue preservation chamber. Such a method is described below with regard to FIGS. 3-9.

Figure 3:
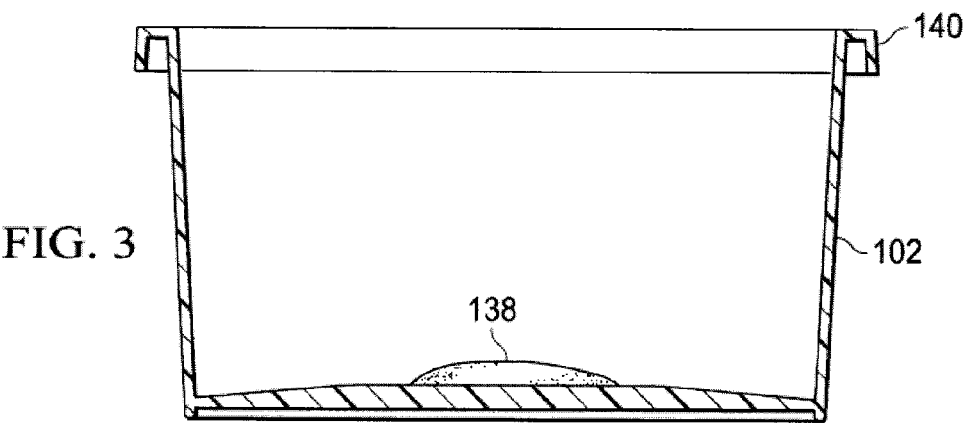
FIG. 3 shows a side, cross-section view of a base of an illustrative embodiment of a tissue preservation chamber, including a piece of tissue.
Figure 4:
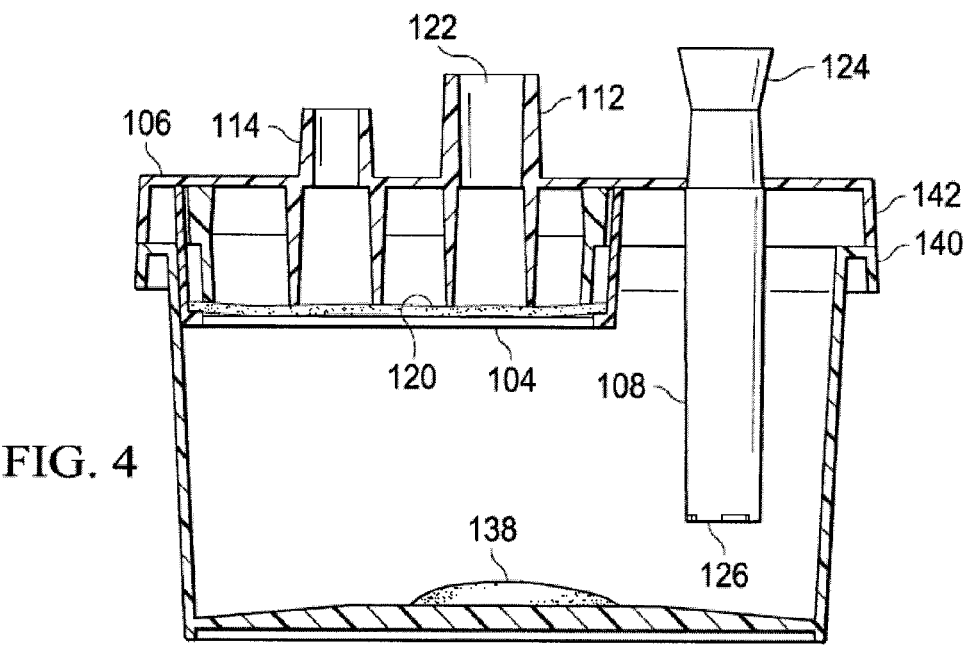
FIG. 4 shows a side, cross-section view of an illustrative embodiment of a tissue preservation chamber, including the base of FIG. 3 and a lid.

In FIG. 3, tissue 138, such as an allograft, is stored in the base 102 of the tissue preservation chamber 100, which is enclosed to form a sealed, sterile environment. After adding the tissue 138, the lid 102 and filter basket 104 may be installed to enclose the tissue preservation chamber 100. For example, a filter 120, such as filter paper, may be placed in the filter basket 104 that is attached to the base 102 or filter basket mount 146 as described above. The lid 106 comprises the media outlet 110, media inlet 114, and gas exchange port 112. The media outlet 110 is coupled to the media outlet conduit 108, the base of which includes a media intake aperture 126 to facilitate the removal of media from the tissue preservation chamber. To help maintain the sterile environment within the tissue preservation chamber 100, a one-way valve 124 is affixed to the media outlet 110 to prevent the unwanted reentry of removed liquids into the tissue preservation chamber 100. The gas exchange port 112 comprises an open conduit 122 that is coupled to the filter 120, which separates the sterile environment of the tissue preservation chamber 100 from the external environment. The media inlet 114 forms a conduit through which tissue preservation media may be added to the tissue preservation chamber 100 after passing through the filter 120.

Figure 5:
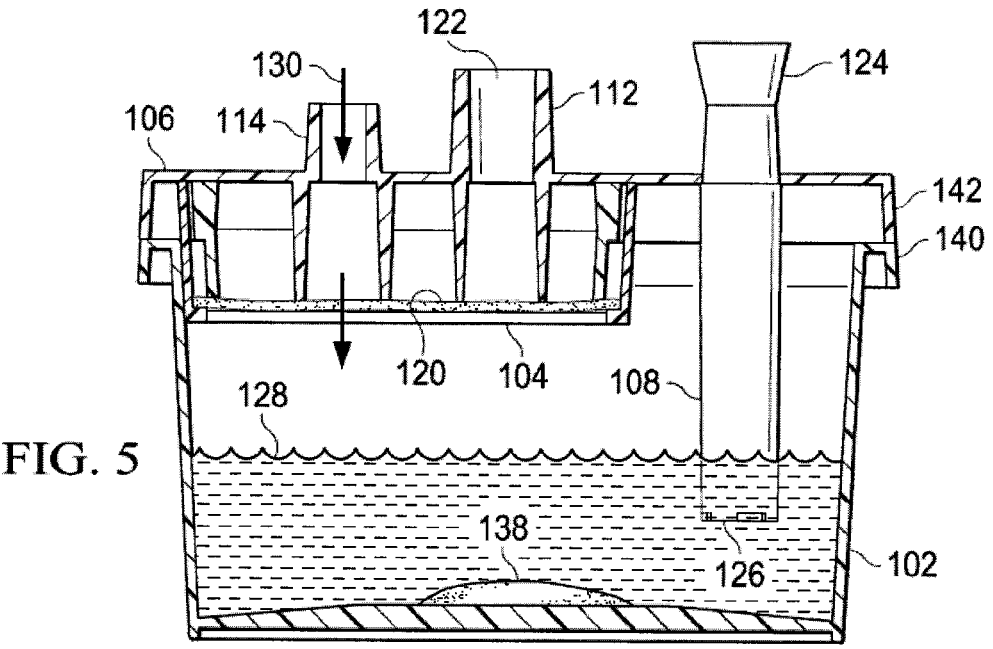
FIG. 5 shows a side, cross-section view of an illustrative embodiment of a tissue preservation chamber, including the flow of media into the tissue preservation chamber.

FIG. 5 shows that liquid 128, such as tissue preservation media, may be added to the tissue preservation chamber 100 to submerge the tissue 138 in the liquid 128. The liquid 128 may be added to the tissue preservation chamber 100 through the media inlet 114 along a fluid flow path indicated by the arrows 130. To maintain the sterile environment within the tissue preservation chamber 100, the liquid 128 is forced into the tissue preservation chamber 100 through the filter 120.

Figure 6:
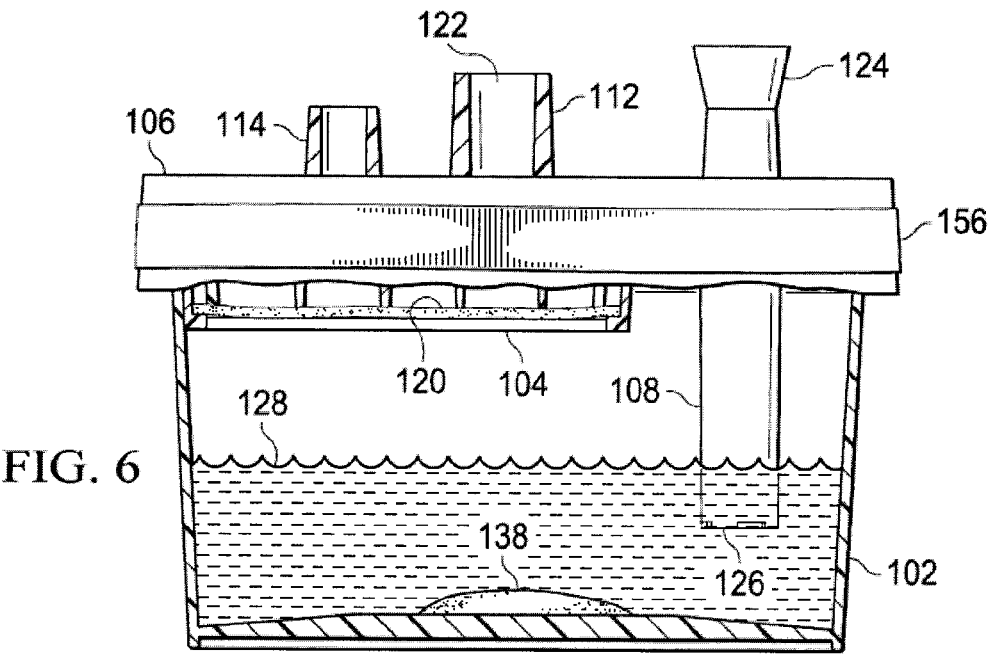
FIG. 6 shows a side view in partial cross-section of an illustrative embodiment of a tissue preservation chamber being used to store and preserve tissue.
Figure 7:
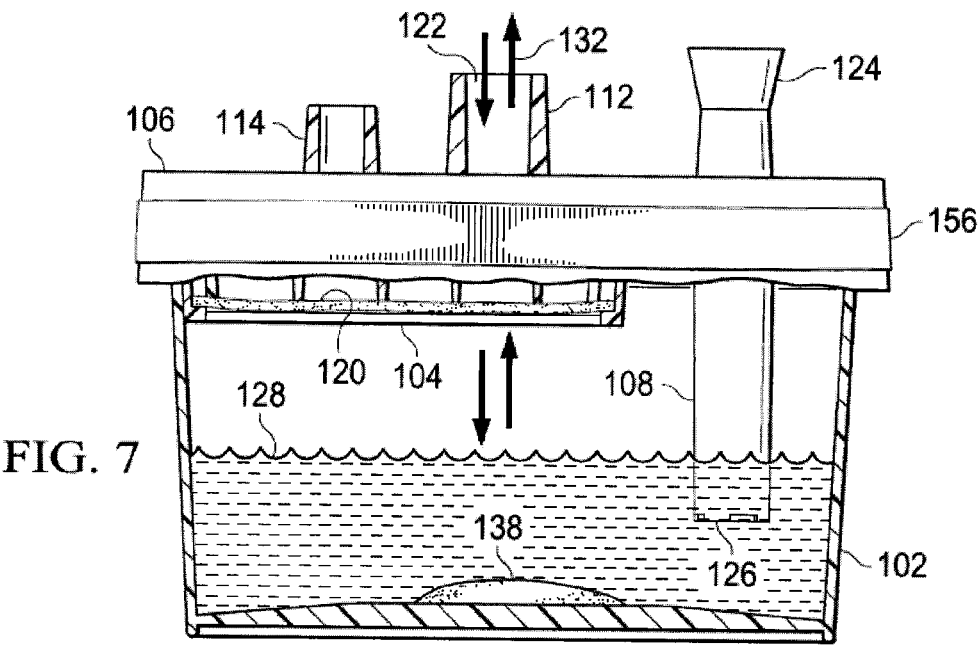
FIG. 7 shows a side view in partial cross-section of an illustrative embodiment of a tissue preservation chamber, including the flow of gas into and out of the chamber.

Sealing tape 156, which may be tamper evident tape, may be applied to the junction of the lid 106 and base 102 about the periphery of the tissue preservation chamber 100, as shown in FIG. 6. The addition of sealing tape 156 helps to ensure the maintenance of a sterile environment within the tissue preservation chamber 100. The tape may also evidence whether the seal has been compromised. As shown in FIG. 7, tissue 138 may be stored in the tissue preservation chamber for the periods described above. During storage, air may flow into and out of the chamber through the gas exchange port 112 and filter 120, as indicated by the two-way arrows 132.

Figure 8:
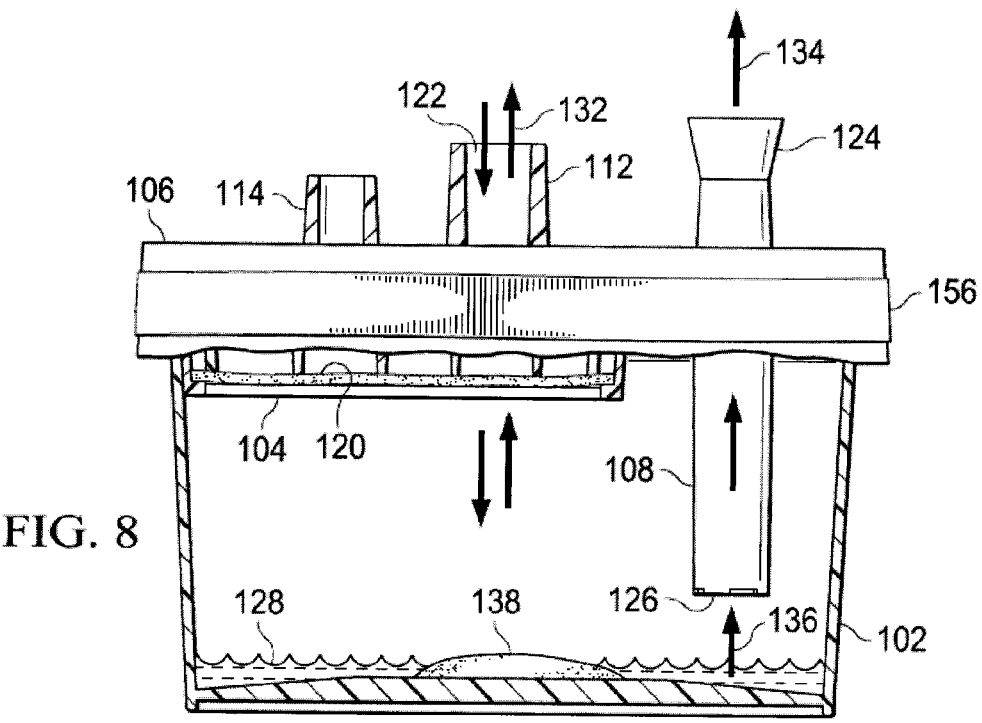
FIG. 8 shows a side view in partial cross-section of an illustrative embodiment of a tissue preservation chamber, including the flow of gas into and out of the tissue preservation chamber and the flow of media out of the tissue preservation chamber.

The liquid 128, e.g., tissue preservation media, may be evacuated from the tissue preservation chamber 100 via the media outlet, as indicated by the arrows 136 of FIG. 8. Further, constant pressure may be maintained within the tissue preservation chamber 100 during the evacuation of fluid 128 by allowing filtered air to enter the chamber via the gas exchange port 112 as the fluid 128 is evacuated. Fluid evacuated from the tissue preservation chamber 100 is prevented from reentering the chamber by one-way valve 124 and is removed from the system as indicated by arrows 134.

Figure 9:
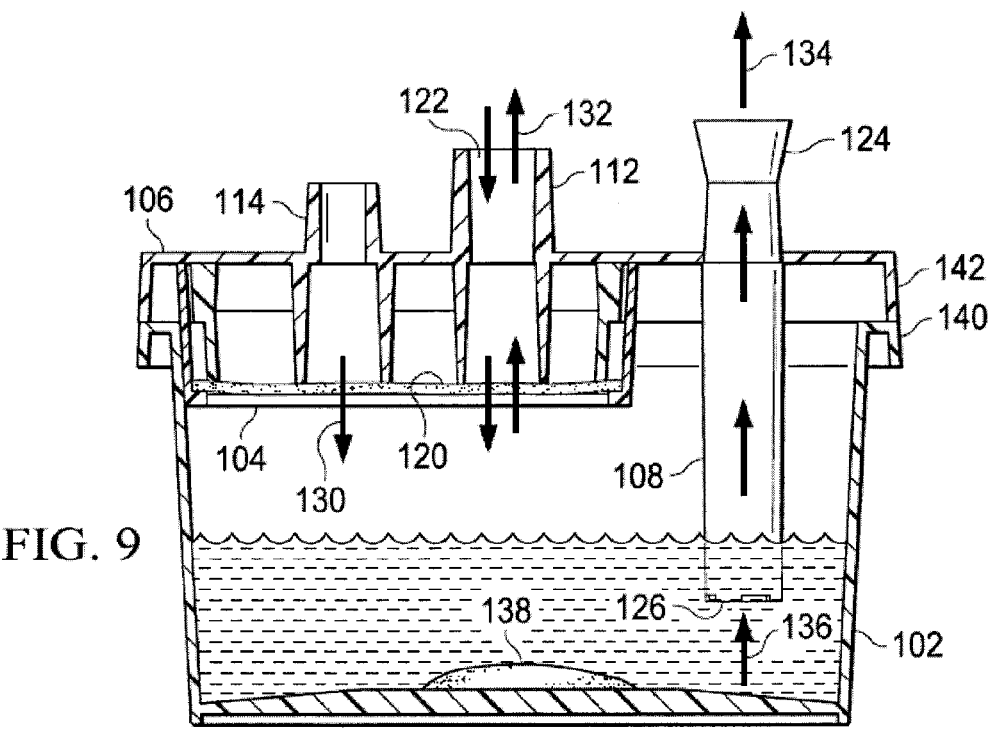
FIG. 9 shows a side, cross-section view of an illustrative embodiment of a tissue preservation chamber, including the flow of media into the chamber, the flow of gas into and out of the chamber, and the flow of media out of the tissue preservation chamber.

As shown in FIG. 9, the liquid 128 may be cycled through the tissue preservation chamber 100 by adding liquid to the chamber through the media inlet 114 and filter 120. Simultaneously or at another time, liquid may be removed from the tissue preservation chamber 100 via the media outlet 110, as indicated by the arrows 134.

EXAMPLES

Example 1

Analysis and Comparison of Osteochondral Allograft Metabolism Using Various Preservation Protocols Tissue Harvest and Culture:

Medial and lateral femoral condyles (FC) from both knees of 10 adult canine cadavers were aseptically harvested within 4 hours of euthanasia performed for reasons unrelated to this study. The volume of each FC was determined and the FCs (n=40) were processed under aseptic conditions and preserved in Media 1 (M-1) (DMEM, 1×ITS (insulin, transferrin, and selenous acid), non-essential amino acids (1 mM), sodium pyruvate (10 mM), and L-ascorbic acid (50 μg/ml)) or Media 2 (M-2) (DMEM, 1×ITS (insulin, transferrin, and selenous acid), non-essential amino acids (1 mM), sodium pyruvate (10 mM), L-ascorbic acid (50 μg/ml), dexamethasone (10 μM), TGF-β3 (2.5 ng/ml), and sodium borate (250 μg/ml)) at 4° C. or 37° C. for 28 or 56 days. The volume of media used for preservation was determined by multiplying the approximate volume of the tissue by 25-30. The media were changed every 7 days, and samples saved for subsequent analyses. In a second study, FCs were aseptically harvested from one knee of 5 adult canine cadavers euthanatized for reasons unrelated to this study. One FC per animal was processed under aseptic conditions and preserved in Media 3 (M-3) (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, amphotericin B, and sodium borate (250 µg/ml)) at 37° C. for 56 days as described above. At each time point, full-thickness cartilage was evaluated for tissue viability.

Media Analysis:

Media were analyzed for nitric oxide (NO) by Griess assay (Promega); PGE2 by ELISA (Cayman Chemical); MMP-2, -3, -9, and -13 by Luminex multiplex assay (R&D System); and IL-2, IL-4, IL-6, IL-7, IL-8, IL-10, IL-15, IL-18, GM-CSF, IP-10, IFNγ, KC, MCP-1, and TNFα by Luminex multiplex assay (Millipore).

Data Analysis:

Data were compared by ANOVA and the Tukey posthoc test using SigmaStat.

Results

Undetected Analytes:

The concentration of MMP-9, IL-2, IL-4, IL-7, IL-10, IL-15, IL-18, GM-CSF, IP-10, IFNγ, and TNFα were all below the detection level of the assay in all samples analyzed for this study, indicating little production of these proteins during culture of OCAs.

4° C. Culture vs. 37° C. Culture:

After day 7, the 4° C. culture groups released significantly ($p<0.05$) less KC, MCP-1, IL-8, MMP-2, MMP-3, and MMP-13. After day 7, production of all of these proteins decreased significantly ($p<0.05$) in the 4° C. culture groups at all time points tested.

The concentration of NO released to the media in the 4° C. group was significantly ($p<0.001$) lower than the M-1 and M-2 37° C. culture groups at days 7 and 28, but not day 56. The M-3 37° C. culture group did not release detectable levels of NO at any time point tested, and therefore release significantly lower NO to the media compared to the 4° C. groups at all time points. The concentration of PGE2 released to the media in the 4° C. group was significantly lower than the M-1 and M-2 37° C. culture groups at all time points tested. The M-3 37° C. culture group released significantly lower PGE2 to the media compared to the 4° C. culture groups at all time points.

M-1 vs. M-2 at 4° C. Culture:

The M-2 4° C. culture group released significantly ($p=0.008$) higher NO on day 7, but not days 28 or 56, compared to the M-1 4° C. culture group. The M-1 4° C. group released significantly higher PGE2 on days 28 ($p<0.001$) and 56 ($p=0.046$), but not day 7, compared to the M-2 4° C. group. There was not a significant difference between the M-1 and M-2 4° C. culture groups for MMP-2, MMP-3, MMP-13, KC, MCP-1, and IL-8 at any time point tested.

M-1 vs. M-2 vs. M-3 at 37° C. Culture:

The M-3 37° C. culture group released significantly ($p<0.05$) lower NO and PGE2 at all time points tested compared to the M-1 and M-2 37° C. culture groups. The M-2 37° C. group released significantly higher NO ($p=0.042$) and PGE2 ($p=0.046$) on day 28, but not ($p>0.05$) days 7 and 56. At days 7 and 28, but not day 56, the M-2 37° C. culture group released significantly ($p<0.05$) lower MMP-2 compared to the M-1 and M-3 37° C. culture groups. At day 7, but not days 28 and 56, the M-1 37° C. group released significantly higher MMP-3 to the media compared to the M-2 and M-3 37° C. culture groups. There was not a significant difference in the media concentration of MMP-13 between any of the 37° C. culture groups at the time points tested. The media concentration of KC decreased significantly over time in culture for all 37° C. groups, but there was not a significant difference between the 37° C. culture groups at any of the time points tested. The media concentration of IL-6 was significantly ($p<0.05$) lower in the M-2 37° C. group compared to the M-1 and M-3 37° C. groups on day 7, but after day 7 the media concentration of IL-6 was below the level of detection for almost all samples. On day 7, but not days 28 and 56, the media concentration of IL-8 was significantly ($p<0.05$) lower in the M-2 37° C. group compared to the M-1 and M-3 37° C. groups. Further, the media concentration of IL-8 decreased significantly ($p<0.05$) over time for all 37° C. culture groups at the time points tested. At all time points tested, the media concentration of MCP-1 was significantly ($p<0.05$) higher in the M-1 37° C. group compared to the M-2 and M-3 37° C. groups. However, the media concentration of MCP-1 decreased significantly ($p<0.05$) over time for all 37° C. culture groups at the time points tested.

Discussion

The media concentrations of the proteins analyzed in this study were very low for tissues cultured at 4° C. after the first week of culture. This indicates that the tissue becomes quiescent under these non-physiologic culture conditions. Conversely, the OCAs cultured at 37° C. maintained a relatively high level of protein production indicating that the chondrocytes remain metabolically active during preservation.

Of the proteins analyzed, MMP-2, MMP-3, KC, MCP-1, and IL-8 were produced most consistently. The stable release of NO and PGE2 to the media throughout the preservation period by tissues stored at 4° C. was a surprising finding. Without being bound by theory, it is possible that the release of these two inflammatory indicators results from the progressive cell death within the tissue and requires very little metabolic activity by the tissue to be produced. The NO and PGE2 data indicate that there is a continued and stable production of these inflammatory mediators during the preservation of the OCAs at 4 and 37° C. in M1 and M2. Importantly, the M-3 media significantly reduced the media levels of these two inflammatory mediators, indicating that M-3 may protect the tissues during culture by decreasing inflammation and potentially improving the health of the OCA.

A potential contributing factor to failure of OCA procedures clinically relates to the viability of the tissue at the time of implantation. Therefore, a biomarker assay that can differentiate between tissues with low and high viability by testing the preservation media prior to implantation would be of great value to tissue banks and the surgeons using them clinically. These data suggest that proteins evaluated in this study are potential markers for assessment of functional viability of OCAs. Taken together with previous work assessing cell viability and matrix composition of preserved OCAs, preservation of osteochondral tissues in Media 3 and 37° C. is likely to allow for preserving higher quality grafts for a longer time period than currently used protocols Example 2

Osteochondral Allograft Preservation in a Serum-Free Chemically-Defined Media

Osteochondral allografts (OCAs) are currently preserved at 4° C. and used within 28 days of donor harvest. The window of opportunity for implantation is limited to 14 days due to a two week disease testing protocol, severely limiting availability to potential recipients. This study was performed to assess the effects of storage up to 56 days in a serum-free chemically defined media at 37° C. OCAs from adult canine cadavers were aseptically harvested within four hours of euthanasia. Medial and lateral femoral condyles were stored in Media 1 or 2 at 4° C. or 37° C. for up to 56 days. Chondrocyte viability, proteoglycan (GAG) and collagen (HP) content, biomechanical properties, and collagen II and aggrecan content were assessed at Days 28 and 56. Five femoral condyles were stored overnight and assessed the next day to serve as controls. Storage in Media 1 at 37° C. maintained chondrocyte viability at significantly higher levels than in any other media-temperature combination examined and at levels not significantly different from controls.

OCAs stored in either media at 4° C. showed a significant decrease in chondrocyte viability throughout storage. GAG and HP content were maintained through 56 days of storage in OCAs in Media 1 at 37° C. There were no significant differences in elastic or dynamic moduli among groups at Day 56. Qualitative immunohistochemistry demonstrated the presence of collagen II and aggrecan throughout all layers of cartilage during storage. OCA viability, matrix content and composition, and biomechanical properties were maintained at "fresh" levels through 56 days of storage in media 1 at 37° C. OCAs stored at 4° C. were unable to maintain viability or matrix integrity through 28 days of storage.

Storage Protocol:

OCAs within 4 hours of death from medial and lateral femoral condyles of adult canine cadavers euthanized for reasons unrelated to this study. Allografts were stored overnight in media at 37° C., 95% humidity, and 5% CO2. Day 0 Control OCAs (n=5) were aseptically harvested from one femoral condyle of 5 adult canine cadavers euthanized for reasons unrelated to this study. These OCAs were stored overnight in serum-free media and evaluated the following day.

The volume of each OCA (n=40) was determined and storage media volumes used were 25-30 times OCA volume. The OCAs were stored in Media 1 (DMEM, 1×ITS (insulin, transferrin, and selenous acid), non-essential amino acids (1 mM), sodium pyruvate (10 mM), and L-ascorbic acid (50 µg/ml)) or Media 2 (DMEM, 1×ITS (insulin, transferrin, and selenous acid), non-essential amino acids (1 mM), sodium pyruvate (10 mM), L-ascorbic acid (50 µg/ml), dexamethasone (10 µM), TGF-β3 (2.5 ng/ml), and sodium borate (250 µg/ml)).

Once the OCAs were aseptically processed they were preserved in either Media 1 or 2 at 4° C. or 37° C. for 28 or 56 days. Media 1 was designed to provide basic nutrition to the tissue and Media 2 was designed to be anti-inflammatory and chondrogenic. Each stored specimen had its own contralateral control on the opposite leg. The media were changed every 7 days and media samples were saved for subsequent analyses. At each time point full-thickness cartilage was evaluated for chondrocyte viability, biochemical composition, and biomechanical properties.

Tissue Viability Analysis:

Full-thickness cartilage from each storage group was used to determine chondrocyte viability. Quantitative analysis of chondrocyte viability was determined by manually counting live and dead cells from images for the entire sample taken at 10× magnification using an Olympus F view II camera and Micro Suite Basic Edition software. CellTracker™ Green CMFDA (5-chloromethylfluorescein diacetate, Invitrogen, Carlsbad, Calif.) was used to visualize live cells and ethidium homodimer-1 (EthD-1, Invitrogen, Carlsbad, Calif.) to visualize dead cells. Percent live cells were determined by taking the total number of live cells divided by the total amount of cells in the sample.

GAG Content:

After PBS wash, cartilage plugs were blotted with a paper wipe and weighed on balance to obtain the wet weight. Dry weight was determined after lyophilization for 24 hours. Cartilage tissue was the then digested in 50 µL papain solution for 3 hours at 60° C. Sulfated-GAG (s-GAG) concentration within the cartilage matrix was determined using aliquots of digest solution using the 1,9 dimethylmethylene blue (DMMB) dye-binding assay. S-GAG content was determined from the ratio of s-GAG to total tissue dry weight and reported at µg GAG/mg dry weight.

HP Content:

The hydroxyproline (HP) content was determined using a colorimetric assay modified to a 96-well format. HP content was used as a measure of total collagen content. A 50-µl, aliquot of the digest solution was mixed with 50 µL 4N NaOH and the mixture was autoclaved for 20 minutes at 121° C. to hydrolyze the sample. The sample was then mixed with the chloramine T reagent and incubated at 25° C. for 25 minutes, followed by mixing with Ehrlich aldehyde reagent. The chlorophore was developed at 65° C. for 20 minutes. The absorbance was then read at 550 nm using a Synergy HT (BioTEK, Highland Park, Vt.) and the samples were compared with an HP standard to determine the HP concentration of the sample. Results were standardized to tissue dry weight and reported as µg HP/mg dry weight.

Biomechanical Analysis:

At each end point, 4-mm plugs were removed from the articular cartilage and immediately put in a −80° C. freezer until biomechanical testing could be done. The dynamic modulus of cartilage specimens were determined by unconfined compression with loading to 10% strain at a rate of 0.05% per second, after an initial 0.02-N tare load (elastic modulus, or Eγ). Dynamic modulus (G*) was measured by superimposing 2% peak-to-peak sinusoidal strain at 0.1 Hz. Values were reported as megapascals (MPa).

Immunohistochemical Analysis:

For immunohistochemical evaluation, 2-mm sagittal sections of OCAs were cut and fixed in 10% formalin. After fixation was complete, samples were decalcified in 10% disodium ethylenediaminetetraacetic (EDTA) acid. After decalcification and subsequent routine histologic processing, each specimen was embedded in paraffin, and sectioned 5 µm through the sagittal plane. For immunohistochemical analysis, unstained sections were deparaffinized in xylene and rehydrated in graded ethanol solutions. The samples were permeabilized with a 0.1% trypsin solution at 36° C. for 60 minutes and then blocked with a 10% bovine serum albumin at 40° C. Slides were incubated overnight at 4° C. in predetermined dilutions of the primary antibodies: collagen type II (rabbit polyclonal antibody, Abcam, Cambridge, UK) and proteoglycan (mouse anti-human antibody, Millipore Corp., Billerica, Mass.).

The next day, slides were rinsed in Tris-buffered saline before being incubated with the secondary antibody. Collagen type II was labeled with goat anti-rabbit fluorescein isothiocyanate (FITC, Millipore Corp., Billerica, Mass.) and proteoglycan was labeled with goat anti-mouse rhodamine (Millipore Corp., Billerica, Mass.). Samples were coverslipped and reviewed using fluorescent light microscopy. Negative controls were used as comparison in which the primary (but not secondary antibody) was omitted from the slides to see if any stain was due to fluorescence aside from the target region. Immunohistochemical images were subjectively assessed.

Statistical Analyses:

Statistical analyses were done using the SigmaStat® computer software program (San Rafael, Calif.). Data were pooled for each endpoint, Day 28 and Day 56, and comparisons were made among the four storage media and Day 0 controls. A one way ANOVA using Tukey post-hoc comparisons was used for statistical analysis with significance set at $p<0.05$.

Results:

Chondrocyte viability of femoral condyle OCAs stored in Media 1 at 37° C. was significantly higher than Media 1 and 2 at 4° C. (p=0.016, p=0.01) at Day 28. At Day 56, Media 1 at 37° C. had significantly higher cell viability than Media 1 at 4° C. (p=0.008) and Media 2 at 4° C. and 37° C. (p=0.015, p=0.023). When comparing stored OCAs to Day 0 controls, controls had significantly higher viability than OCAs in Media 1 and 2 at 4° C. (p=0.007, p=0.01) at Day 28. OCAs stored in Media 1 at 37° C. were the only group able to maintain viability at levels not significantly different that controls through Day 56. Chondrocyte viability in control OCAs was significantly higher than OCAs in Media 1 at 4° C. (p=0.032) and Media 2 at 4° C. (p<0.001) and 37° C. (p=0.002) at Day 56.

Analysis of tissue GAG content of femoral condyle OCAs showed no significant differences among storage groups at Day 28. At Day 56, OCAs stored in Media 2 at 37° C. had significantly less tissue GAG content than Media 1 at 4° C. (p=0.027) and 37° C. (p=0.033). At Day 28, there were no significant differences in tissue GAG compared to controls. However, at Day 56, controls had significantly more tissue GAG content than OCAs stored in Media 2 at 37° C. (p=0.003).

There were no significant differences among femoral condyle OCA storage groups with respect to HP content at Days 28 or 56. Also, there were no significant differences at any time point compared to controls. Biomechanical analyses of femoral condyle OCAs showed elastic modulus of controls to be significantly higher than OCAs in Media 1 at 37° C. (p=0.017) and Media 2 at 4° C. (p=0.016) at Day 28. Dynamic modulus was significantly higher in controls than OCAs in Media 1 at 4° C. (p=0.032) and 37° C. (p=0.022) as well as Media 2 at 4° C. (p=0.041) at Day 28. There were no significant differences noted for Day 56 analyses.

Example 3

Assessment of Potential Biomarkers for Evaluating Viability of Osteochondral Allograft Tissue During Preservation Osteochondral allografts (OCA) allow transplantation of viable, functional tissue for treatment of cartilage defects without the need for immunosuppression. OCAs are reported to be successful in >75% of cases when used for treatment of focal femoral condyle lesions. The present study was designed to evaluate the ability of biomarkers to differentiate OCAs with low viability during culture using various tissue preservation protocols.

Tissue Harvest and Culture:

Medial and lateral femoral condyles (FC) from both knees of 10 adult canine cadavers were aseptically harvested within 4 hours of euthanasia performed for reasons unrelated to this study. The volume of each FC was determined and the FCs (OCAs, n=40) were processed under aseptic conditions and preserved in Media 1 (M-1) or Media 2 (M-2) at 4° C. or 37° C. for 28 or 56 days. The volume of media used for preservation was determined by multiplying the approximate volume of the tissue by 25-30. The media were changed every 7 days, and collected for analysis of biomarker production. In a second study, the FCs were aseptically harvested from one knee of 4 adult canine cadavers euthanatized for reason unrelated to this study.

One FC per animal was processed under aseptic conditions and preserved in Media 3 (M-3) (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, amphotericin B, and sodium borate (250 μg/ml)) at 37° C. for 56 days as described above. At each time point, full-thickness cartilage was evaluated for tissue viability.

Tissue Viability Analysis:

Cartilage tissue was analyzed for cell viability using a fluorescent live/dead assay (Invitrogen) and fluorescent microscopy. Images were taken at 10× magnification using an Olympus F-View II camera and MicroSuite Basic Edition software. For the M-1 and M-2 samples, two tissue sections were used for evaluation of tissue viability. For the M-3 samples at least three tissue sections were taken for evaluation of tissue viability. Green-staining live cells were manually counted and the area of the tissue analyzed was determined using MicroSuite Basic Edition. Because % cell viability does not take into account total loss of cells, the area of the tissue section analyzed was measured, and the ratio of live cells (LC)/area (mm2) was determined.

Media Analysis:

Media were analyzed for MMP-2, -3, and -13 (R&D System) and IL-8, KC, and MCP-1 (Millipore) using two Luminex multiplex assay.

Data Analysis:

Data were compared by Pearson product-moment correlation using SigmaStat.

Tissue Viability (Table 1):

The mean tissue viability represented the viability of each group well, but each group had one outlier. Further, the viabilities of M-2-37 and M-3-37 were significantly higher than all other groups. Because the response of the OCAs to each preservation protocol was unique, the media protein data were analyzed to determine if the outliers could be identified in each group.

All 4° C. Culture Groups:

After day 14, the only analytes tested that were consistently detected were MMP-3 and KC, and the concentrations of these proteins were significantly lower than the day 7 values at all time points. Further, a difference in the media concentration could not be determined between the OCAs with the lowest tissue viability (0.23 LC/mm2 M-1, 0.093 LC/MM2 M-2) and the highest tissue viability (1.14 LC/MM2 M-1, 0.747 LC/MM2 M-2).

M-1 37° C. Culture Groups:

The variability in the tissue viability of the M-1 group was relatively low, and the viability of the tissues was relatively high. Therefore, there was not a distinct difference in the biomarker values of the samples with low viability (~0.7 LC/mm2) and high viability (≥1.0 LC/mm2). Interestingly, there was a negative weak to moderate correlation between cell viability and all the biomarkers analyzed in this study.

M-2 37° C. Culture Groups:

The tissue viability of this group was significantly lower than the other 37° C. groups. After day 7 the concentration of KC and IL-8 had moderate-strong positive correlations (0.569-0.995) with tissue viability depending on the day analyzed. MCP-1 had weak-moderate (0.339-0.613) positive correlations with tissue viability throughout the culture period. MMP-2, MMP-3, and MMP-13 all had a moderate-strong (0.651-0.927) positive correlations on days 7 and 28, and a weak-moderate (0.337-0.6) positive correlations on day 56. The two samples with the lowest tissue viability (<0.1 LC/mm2) had little to no detectable KC, IL-8, MCP-1, MMP-2, MMP-3, and MMP-13 after day 7.

M-3 37° C. Culture Groups:

The M-3 group had the largest disparity between the samples with the highest (>1.0 LC/mm2) viability (n=3) and lowest (0.00 LC/mm2) viability (n=1). After day 14, little to no MCP-1, IL-8, and KC detectable in the media of the low viability sample. Early in culture, KC and MCP-1 had strong (0.815-0.972) positive correlations to tissue viability, and at later time points in culture each had moderate (0.5-0.78) positive correlations to tissue viability. At all time points, IL-8 had moderate (0.566-0.751) positive correlations to cell viability. MMP-2 had strong (0.811-0.907) positive correlations through day 21; MMP-3 had strong (0.889-0.968) positive correlations after day 7; and MMP-13 had weak (0.3-0.461) positive correlations to tissue viability at all time points. The sample with the lowest tissue viability (0.00 LC/mm2) had little to no detectable KC, IL-8, and MCP-1 after day 7, but MMP-2, MMP-3, and MMP-13 could be detected at all time points.

These data indicate that proteins in the preservation media have the potential to act as biomarkers for distinguishing OCAs that have very low cell viability and therefore are not considered suitable for clinical use. If implemented, tissue banks could readily and repeatedly assess the usefulness of the tissue during the preservation period without the need for sectioning the grafts. This would essentially allow tissue banks to cull samples as soon as they are no longer acceptable for clinical use, saving time and expense. It would also allow surgeons to have more confidence in the quality of the grafts that they are implanting into patients. KC, MCP-1, and MMP-3 are the strongest candidate biomarkers to identify OCAs with low tissue viability during culture.

TABLE I

Tissue viability for each tissue preservation protocol

| Media | Storage Temp (C.) | Days In Storage | Tissue Viability (LC/mm2) Mean | Range |
| --- | --- | --- | --- | --- |
| M-1 | 4 | 28 | 0.57 | 0.245-1.088 |
| M-1 | 4 | 56 | 0.41 | 0.112-1.143 |
| M-1 | 37 | 28 | 1.05 | 0.819-1.24 |
| M-1 | 37 | 56 | 1.03 | 0.736-1.32 |
| M-2 | 4 | 28 | 0.5 | 0.033-0.892 |
| M-2 | 4 | 56 | 0.37 | 0.093-0.747 |
| M-2 | 37 | 28 | 0.6 | 0.110-0.882 |
| M-2 | 37 | 56 | 0.36 | 0.009-0.628 |
| M-3 | 37 | 56 | 1.32 | 0.00-1.44 |

Example 4

Optimization of Osteochondral Allograft Preservation to Extend the Usable Life Span of Harvested Tissue The present study was designed to evaluate the effectiveness of culturing OCAs at 37° C. using different media compositions for extending the pre-implantation life span of harvested tissue based on tissue viability and matrix composition.

Methods

Tissue Harvest and Culture:

Medial and lateral femoral condyles (FC) from both knees of 10 adult canine cadavers were aseptically harvested within 4 hours of euthanasia performed for reasons unrelated to this study. The volume of each FC was determined and the FCs (OCAs, n=40) were processed under aseptic conditions and preserved in Media 1 (M-1) or Media 2 (M-2) at 4° C. or 37° C. for 28 or 56 days. The volume of media used for preservation was determined by multiplying the approximate volume of the tissue by 25-30. The media were changed every 7 days, and saved for subsequent analyses. In a second study, FCs were aseptically harvested from one knee of 5 adult canine cadavers euthanatized for reason unrelated to this study. One FC per animal was used as a freshly harvested day 0 control (n=5), and the other was processed under aseptic conditions and preserved in Media 3 (M-3) (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, amphotericin B, and sodium borate (250 μg/ml)) at 37° C. for 56 days as described above. At each time point, full-thickness cartilage was evaluated for tissue viability, proteoglycan (GAG) content, and collagen (HP) content.

Viability Analysis:

Cartilage tissue was analyzed for cell viability using a fluorescent live/dead assay (Invitrogen) and fluorescent microscopy. For the M-1, M-2, and Day 0 control tissues full thickness cartilage was excised from the bone; two 4 mm cartilage plugs were created from the tissue using a dermal punch; a ~0.5 mm thick slice was taken from the middle of the plug, and the slice was stained for 30 minutes at 37° C. For the M-3 tissues a diamond saw was used to make a 0.5 mm section from the center of the FC and this section was then stained for 30 minutes at 37° C. Images were taken at 10× magnification using an Olympus F view II camera and MicroSuite Basic Edition software. For the M-1, M-2, and Day 0 samples one image from each slice (n=2 images) was used for evaluation of tissue viability. For the M-3 samples, at least 3 images from different areas of the slice were used for evaluation of tissue viability. Greenstaining live cells were manually counted and the area of the tissue analyzed was determined using MicroSuite Basic Edition. Because % cell viability does not take into account total loss of cells, the area of the tissue section analyzed was measured, and the ratio of live cells (LC)/area (mm2) was determined.

Biochemical Analyses:

Tissue GAG content was determined using the dimethylmethylene blue assay. Tissue HP content was determined using the hydroxyproline assay. Tissue GAG and HP content was standardized to tissue dry weight.

Data Analysis:

Data were compared by ANOVA and the Tukey post-hoc test using SigmaStat.

Results

Tissue Culture:

One sample in the M-2-37-56 group and M-3-37-56 group was lost to processing problems. Therefore, these groups only had 4 samples for analysis.

Figure 10:
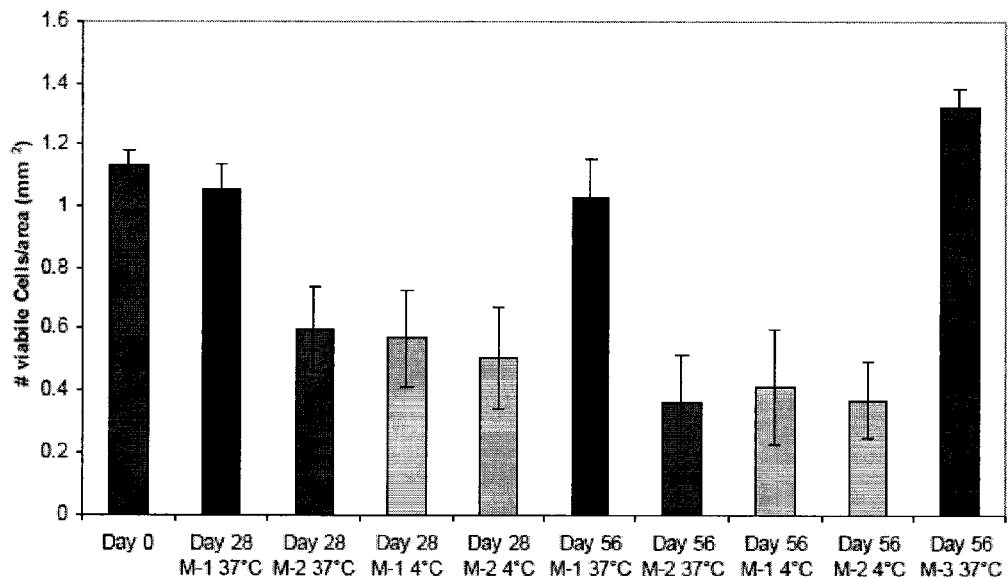
FIG. 10 shows tissue viability at days 1, 28, and 56.

Tissue Viability (FIG. 10):

The mean tissue viability of the day 0 controls was 1.13 LC/mm2 (1.03-1.25 LC/mm2). The tissue viability of the M-1-37 group was not significantly different than day 0 group at day 28 or 56. There was not a significant difference between the M-3-37-56 group and the day 0 control for tissue viability. The M-1-4, M-2-4, and M-2-37 groups all had significantly lower tissue viability compared to the day 0 control ($p<0.005$-$0.008$), the M-1-37 group ($p<0.016$-$0.025$), and M-3-37 group ($p<0.004$-$0.006$) at all time points. There was not a significant difference between the M-1-37 and M-3-37 groups.

Figure 11:
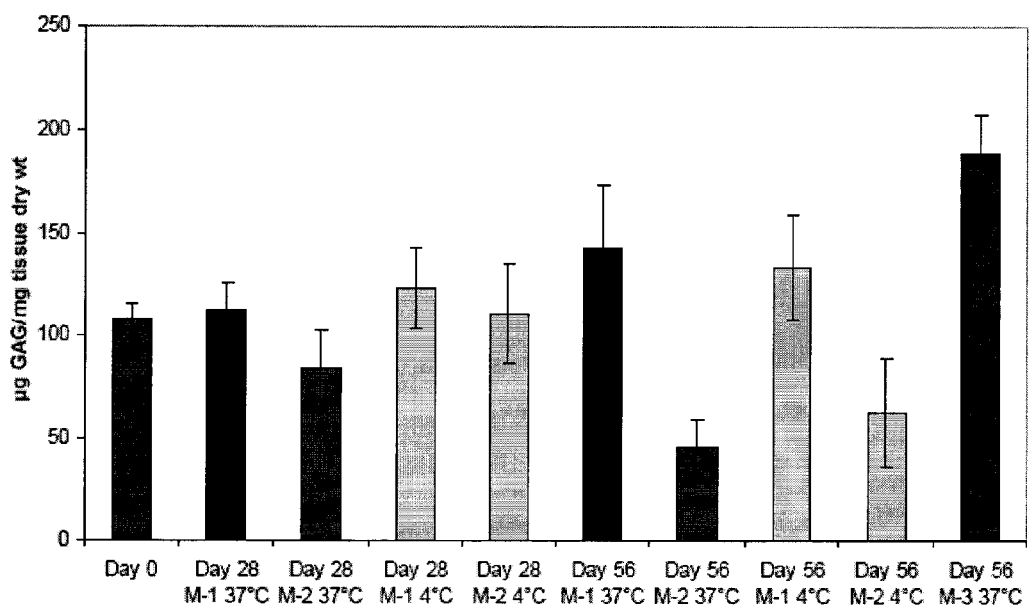
FIG. 11 shows tissue proteoglycan content at days 0, 28, and 56.

Tissue Matrix Composition:

On day 56 the M-2-37 group had significantly ($p<0.003$-$0.027$) lower tissue GAG content compared to the day 0, both M-1 groups, and the M-3-37 group (FIG. 11). Further, the M-2-4 group had significantly ($p<0.01$) lower tissue GAG content compared to the M-3-37-56 group. There were no other significant differences for tissue GAG content. There was not a significant difference in the collagen content of the tissues between any groups at any time point based on HP analysis.

Example 5

Analysis of Osteochondral Allograft Metabolism Using Various Preservation Protocols at 25° C.

Osteochondral allografts (OCA) allow transplantation of viable, functional tissue for treatment of cartilage defects without the need for immunosuppression. Currently, tissue banks store OCAs at 4° C. and recommend implantation within 28 days of harvest. The present study was designed to evaluate the effects of various tissue preservation protocols on the metabolism of OCAs based on the release of degradative enzymes, cytokines, and chemokines to the media at 25° C. previously shown to be released during 37° C. storage.

Methods

Tissue Harvest and Culture:

During the course of two studies, medial and lateral femoral condyles (FC) from both knees of 14 adult canine cadavers were aseptically harvested within 4 hours of euthanasia performed for reasons unrelated to this study. The FCs were separated into one of 5 test groups based on different media composition (M-1 (DMEM, 1×ITS (insulin, transferrin, and selenous acid), L-glutamine (20 mM), non-essential amino acids (1 mM), sodium pyruvate (10 mM), L-ascorbic acid (50 µg/ml), penicillin, streptomycin, and amphotericin B), M-2 (DMEM, 1×ITS (insulin, transferrin, and selenous acid), L-glutamine (20 mM), non-essential amino acids (1 mM), sodium pyruvate (10 mM), L-ascorbic acid (50 µg/ml), penicillin, streptomycin, amphotericin B, and sodium borate (250 µg/ml)), M-3 (DMEM, 1×ITS (insulin, transferrin, and selenous acid), L-glutamine (20 mM), non-essential amino acids (1 mM), sodium pyruvate (10 mM), L-ascorbic acid (50 µg/ml), penicillin, streptomycin, amphotericin B, and dexamethasone (0.01 µM))) and container condition (C-1, C-2, C-3) such that each FC from a single animal was placed in a distinct group. The following media and container condition groupings were assessed for this study M-1/C-1, M-1/C-2, M-1/C-3, M-2/C-1, and M-3/C-3, resulting in the 5 different OCA storage groups. Tissues were stored at 25° C. without $CO_2$ supplementation in 60 mls of media for at least 63 days and up to 75 days. The media were changed every 7 days and saved for biomarker analyses.

Media Analysis:

Media were analyzed for VEGF, matrix metalloproteinase (MMP)-2, -3, -9, and -13 by Luminex multiplex assay (R&D System); and IL-6, IL-8, KC, and MCP-1 by Luminex multiplex assay (Millipore).

Data Analysis:

Data from days 7, 28, and 56 of storage were compared by ANOVA and the Tukey post-hoc test using SigmaStat.

Results

MMP-2:

The release of MMP-2 to the media increased in all groups after day 7, and remained stable from day 14 to the end of storage in the M-1/C-2 and M-1/C-3 groups of study 1 and the M-1/C-1, M-1/C-3, and M-3/C-3 of study 2. The M-1/C-1 and M-2/C-1 groups in study 1 had decreasing levels of MMP-2 released to the media over time in culture after day 21, and on days 28 and 56 the M-1/C-3 had significantly higher media MMP-2 levels compared to the M-1/C-1, M-1/C-2, and M-2/C-1 groups. In study 2 the M-3/C-3 group had significantly lower MMP-2 compared to the M-1/C-3 group on days 28 and 56, and the M-1/C-1 group on day 28.

MMP-3:

After day 7 all groups in study 1 and the M-1/C-1 group in study 2 released decreasing levels of MMP-3 to the media. However, the level of MMP-3 in the M-1/C-3 group of study 1 remained stable after day 14 and throughout culture for the M-1/C-3 and M-3/C-2 group in study 2. On day 28 of study 1, the M-2/C-1 group had significantly lower media MMP-3 levels compared to the M-1/C-1 and M-1/C-3 group, and on day 56 of study 1 the M-1/C-3 group had significantly higher media MMP-3 levels compared to all other groups. In study 2 the level of MMP-3 was not significantly different between any groups at the time points analyzed.

MMP-9:

MMP-9 was not detected at any time point tested in both study 1 and study 2.

MMP-13:

In study 1 the level of MMP-13 in the media increased quickly after day 7 in the M-1/C-1 and M-1/C-2 groups, and more slowly in the M-1/C-3 and M-2/C-1 groups. On day 28 the M-1/C-3 group had significantly lower media MMP-13 compared to the M-1/C-1 and M-1/C-2 groups. In study 2 the M-3/C-3 group had significantly lower media MMP-13 levels compared to the M-1/C-1 and M-1/C-3 groups on day 7 and 28, and the M-1/C-1 group on day 56.

KC:

In study 1 the level of KC in the media was stable in the M-1/C-3, but decreased significantly in all other groups over time in storage. In study 2 the level of KC decreased significantly after day 7 in all groups over time. In study 1, the media level of KC in the M-2/C-1 group was significantly lower than the M-1/C-2 and M-1/C-3 groups on day 7, all groups on days 28 and 56. In study 2, the media level of KC was significantly lower than in the M-3/C-3 group compared to the M-1/C-3 group on days 28 and 56.

IL-6:

In study 1 and study 2 the media level of IL-6 spiked at day 7 and decreased significantly and rapidly in all samples on subsequent days. In study 1 the M-2/C-1 group had significantly lower media IL-6 on day 7 compared to all other groups, and the M-1/C-3 group had significantly higher IL-6 on day 56 than all other groups. In study 2 the M-3/C-3 group had significantly lower media IL-6 compared to the M-1/C-1 and M-1/C-3 group on day 28 and 56.

IL-8:

In study 1 the media level of IL-8 was relatively stable over time in all groups but the M-2/C-1 group, which had decreasing medial IL-8 levels over time in storage. In study 2 the level of IL-8 decreased over time in culture in all groups. In study 1 the M-2/C-1 group had significantly lower media IL-8 levels compared to all groups at all time points analyzed. Further, the M-1/C-3 group had significantly higher media IL-8 levels compared to all other groups on day 56. In study 2 the M-3/C-3 group had significantly lower media IL-8 levels compared to the M-1/C-3 group at all time points and the M-1/C-1 group on days 28 and 56.

MCP-1:

In study 1 the media level of MCP-1 decreased after day 14 and stabilized in all groups but the M-2/C-1 group, which had low MCP-1 media levels from day 7 through day 56 of culture. In study 2 the media level of MCP-1 decreased after day 28 in culture in all groups. In study 1 the media concentration of MCP-1 in the M-2/C-3 group was significantly lower than all other groups on days 28 and 56. Further, the M-1/C-3 group had significantly higher media MCP-1 compared to the M-1/C-1 group on days 28 and 56. In study 2 the media concentration of MCP-1 in the M-3/C-3 group was significantly lower than the M-1/C-3 group on day 56 of storage.
VEGF:
In study 1 the media level of VEGF was stable over time in the M-1/C-3 group, but decreased over time in all other groups. In study 2 the level of VEGF was stable in all groups over time in culture. In study 1 the M-2/C-1 group had significantly lower media VEGF concentrations compared to all groups on day 7 and the M-1/C-2 and M-1/C-3 groups on day 56. In study 2 the M-3/C-3 group had significantly lower media VEGF concentrations compared to the M-1/C-3 group at all time points and the M-1/C-1 group on days 7 and 28.
Discussion
These data indicate that OCA tissues are metabolically active during 25° C. storage, and that the same proteins detected in previous studies at 37° C. storage are also detected at 25° C. storage. Further, the pattern of production of these biomarkers at 25° C. is similar to that observed at 37° C.

Example 6

Optimization of Long-Term Osteochondral Allograft Storage at 25° C.

Figure 12:
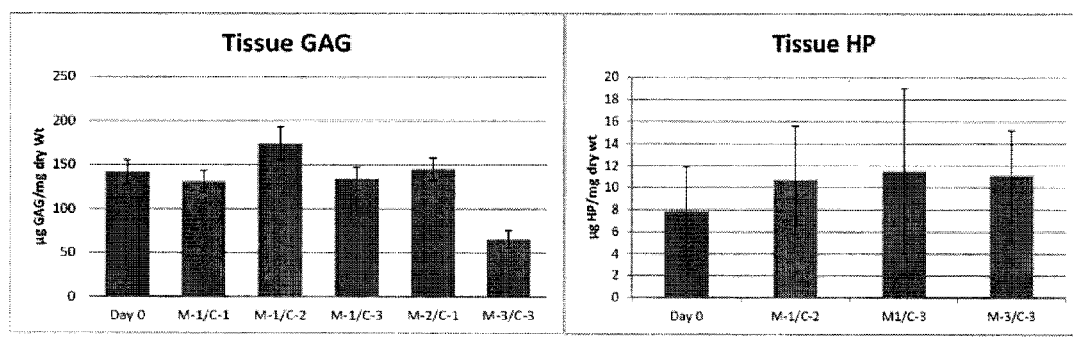
FIG. 12 shows tissue proteoglycan GAG/mg tissue dry weight) and Collagen (μg HP/mg tissue dry weight) content at day 0 and days 63-75 for each OCA storage group.

Osteoarthritis (OA) affects ~90% of people older than 65, and associated costs top $100 billion annually in the U.S. One treatment available for focal lesions is osteochondral allografts (OCA) transplantation. OCAs are reported to be successful in >75% of cases when used for treatment of focal femoral condyle lesions. Currently, tissue banks store OCAs at 4° C., and implantation is recommended within 28 days after harvest due to significant loss in tissue viability by this time point. Because mandatory disease screening protocols typically take 14 days to complete, the window for surgical implantation is narrow (~14 days), which severely limits clinical use. Therefore, this study was designed to evaluate the effectiveness of culturing OCAs at 25° C. using novel media compositions and container conditions for extending the pre-implantation life span of harvested tissue based on tissue viability and matrix composition.
Methods:
Tissue Harvest and Culture:
During the course of two studies, medial and lateral femoral condyles (FC) from both knees of 14 adult canine cadavers were aseptically harvested within 4 hours of euthanasia performed for reasons unrelated to this study. The FCs were either used as day 0 controls (n=7) or separated into one of 5 test groups based on different media composition (M-1 (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, and amphotericin B), M-2 (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, amphotericin B, and sodium borate (250 μg/ml)), M-3 (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, amphotericin B, and dexamethasone (0.01 μM))) and container condition (C-1, C-2, C-3) such that each FC from a single animal was placed in distinct group. The following media and container condition groupings were assessed for this study M-1/C-1, M-1/C-2, M-1/C-3, M-2/C-1, and M-3/C-3, resulting in the 5 different OCA storage groups. Tissues were stored at 25° C. without CO2 supplementation in 60 mls of media for at least 63 days and up to 75 days. The media were changed every 7 days and saved for biomarker analyses. At the end of storage, osteochondral plugs were evaluated for tissue viability and matrix composition.
Viability Analysis:
Cartilage tissue was analyzed for cell viability using a fluorescent live/dead assay (Invitrogen) and fluorescent microscopy. Osteochondral tissues were incubated in stain for 25 minutes at 25° C. Images were taken at either 4× (study 1) or 10× (study 2) magnification. Green-staining live cells were manually counted, and the area of the tissue analyzed was determined. The viability of the tissue is expressed as the ratio of live cells (LC)/area ($\mu m^2$). Because the focal depth of 4× images was significantly different than the focal depth of 10× images, the viability could not be compared between the 4× and 10× images, and analysis was only performed between samples that were taken at the same magnification.
Matrix Composition:
Cartilage tissue was lyophilized and weighed, digested with papain, and analyzed for proteoglycan content using the DMMB assay and collagen content using a hydroxyproline assay. GAG and collagen content was normalized to tissue dry weight.
Data Analysis:
Data were compared by ANOVA and the Tukey post-hoc test using SigmaStat.
Results: Day 0 and Day 63-75 Tissue Viability (Table 2):
The mean tissue viability and range are listed for each group at day 63 for each magnification. For the samples analyzed at 4× magnification, day 0 and the M-3/C-3 group had significantly higher tissue viability (LC/mm2) compared to the M-1/C-1 and M-2/C-1 groups at day 63, and the M-1/C-3 group had significantly higher tissue viability compared to the M-2/C-1 group at day 63. The M-3/C-3 group had the highest mean viability and the lowest variability of all the storage groups tested. The sample size was smaller for the 10× magnification groups, and there was not a significant difference between the groups as seen in the first set of samples analyzed at 4× magnification. However, in agreement with the 4× data, the M-3/C-3 group had the highest viability with the lowest variability and was closest to day 0 viability values.
Day 0 and Day 63-75 Cell Distribution:
The day 0 and M-3/C-3 groups had good cell numbers distributed through the thickness of the tissue. The M-1/C-1 and M-1/C-2 groups typically had very low cell numbers in the superficial-middle zones of the tissue and higher cell numbers in the deep-middle zones of the tissue. The M-2/C-1 group had very few detectable viable cells in any region of the tissue.
Matrix Composition (FIG. 12):
The proteoglycan content of the M-3/C-3 group was significantly lower than the day 0 and all other storage groups. The GAG content of the tissues was not a significantly different between any other groups in this study. The HP content of the first set of tissues stored could not analyzed for HP content, so there is no HP data for the M-1/C-2 and M-2/C-1 groups tissues. Of the samples tested, there was not a significant difference between the groups tested.
Discussion:
These data indicate that femoral condyle OCA tissue stored at 25° C. without CO2 supplementation can maintain day 0 tissue viability up to 75 days in storage. This is a significant improvement over current protocols at 4° C., which shows significant loss of tissue viability by day 28 of storage.

TABLE 2

Tissue viability for each tissue protocol

| Media | Container Condition | 4x Tissue Viability (LC/μm2) Mean | 4x Tissue Viability (LC/μm2) Range | 10x Tissue Viability (LC/μm2) Mean | 10x Tissue Viability (LC/μm2) Range |
|---|---|---|---|---|---|
| M-1 | C-1 | 0.916 | 0.038-3.24 | 0.623 | 0.0-1.38 |
| M-1 | C-2 | 2.115 | 1.29-2.62 | | |
| M-1 | C-3 | 2.217 | 0.1-3.49 | 0.804 | 0.213-1.36 |
| M-2 | C-1 | 0.0423 | 0.0-0.117 | | |
| M-3 | C-3 | 3.195 | 2.99-3.31 | 1.137 | 0.97-1.29 |
| Day 0 | | 2.901 | 0.5-5.35 | 1.13 | 1.02-1.25 |

Example 7

Evaluation of Osteochondral Allograft Viability During Preservation at 25° C.

Osteochondral allografts (OCA) allow transplantation of viable, functional tissue for treatment of cartilage defects without the need for immunosuppression. OCAs are reported to be successful in >75% of cases when used for treatment of focal femoral condyle lesions. This study was designed to evaluate the ability of biomarkers and the media additive to differentiate OCAs with low viability during culture using various tissue preservation protocols at 25° C.

Methods

Tissue Harvest and Culture:

During the course of two studies, medial and lateral femoral condyles (FC) from both knees of 14 adult canine cadavers were aseptically harvested within 4 hours of euthanasia performed for reasons unrelated to this study. The FCs were separated into one of 5 test groups based on different media composition (M-1 (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, and amphotericin B), M-2 (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, amphotericin B, and sodium borate (250 μg/ml)), M-3 (DMEM, 1×ITS (insulin, transferrin, and selenous acid), L-glutamine (20 mM), non-essential amino acids (1 mM), sodium pyruvate (10 mM), L-ascorbic acid (50 μg/ml), penicillin, streptomycin, amphotericin B, and dexamethasone (0.01 μM))) and container condition (C-1, C-2, C-3) such that each FC from a single animal was placed in a distinct group. The following five media and container condition groupings were assessed for this study: M-1/C-1, M-1/C-2, M-1/C-3, M-2/C-1, and M-3/C-3. Tissues were stored at 25° C. without CO2 supplementation in 60 mls of media for at least 63 days and up to 75 days. The media were changed every 7 days and saved for biomarker analyses. On the next to last day of storage, 6 mls of the cell viability media additive as added to each sample and incubated for 24 hours. After 24 hours, a media sample was analyzed for level of fluorescence at a standard sensitivity. Increased fluorescence in the media is indicative of cell metabolism and viability.

Media Analysis:

Media were analyzed for VEGF, matrix metalloproteinase (MMP)-2, -3, -9, and -13 (R&D System); and IL-6, IL-8, KC, and MCP-1 by Luminex multiplex assay (Millipore).

Tissue Viability Analysis:

Cartilage tissue was analyzed for cell viability using a fluorescent live/dead assay (Invitrogen) and fluorescent microscopy. Images were taken at 4× magnification using an Olympus F-View II camera and MicroSuite Basic Edition software. Greenstaining live cells were manually counted, and the area of the tissue analyzed was determined using MicroSuite Basic Edition. The area of the tissue section analyzed was measured, and the ratio of live cells (LC)/area (μm2) was determined.

Data Analysis:

Data from the last day of storage were compared by Pearson product-moment correlation using SigmaStat. Since the M-3 media was designed to decrease tissue inflammation, the cytokines and chemokines analyzed in this study were significantly lower in this group compared to all others during the course of storage. Therefore, the M-3 media cytokine data could not be analyzed with the other media compositions used in this study, but the MMP and media supplement data were used for analysis.

Results

Tissue Viability:

The mean tissue viability represented the viability of each group well, but each group had one outlier except the M-2/C-1 group and the M-3/C-3 group. Further, the viabilities of M-1/C-3 and M-3/C-3 groups were significantly higher than all other groups.

Figure 13:
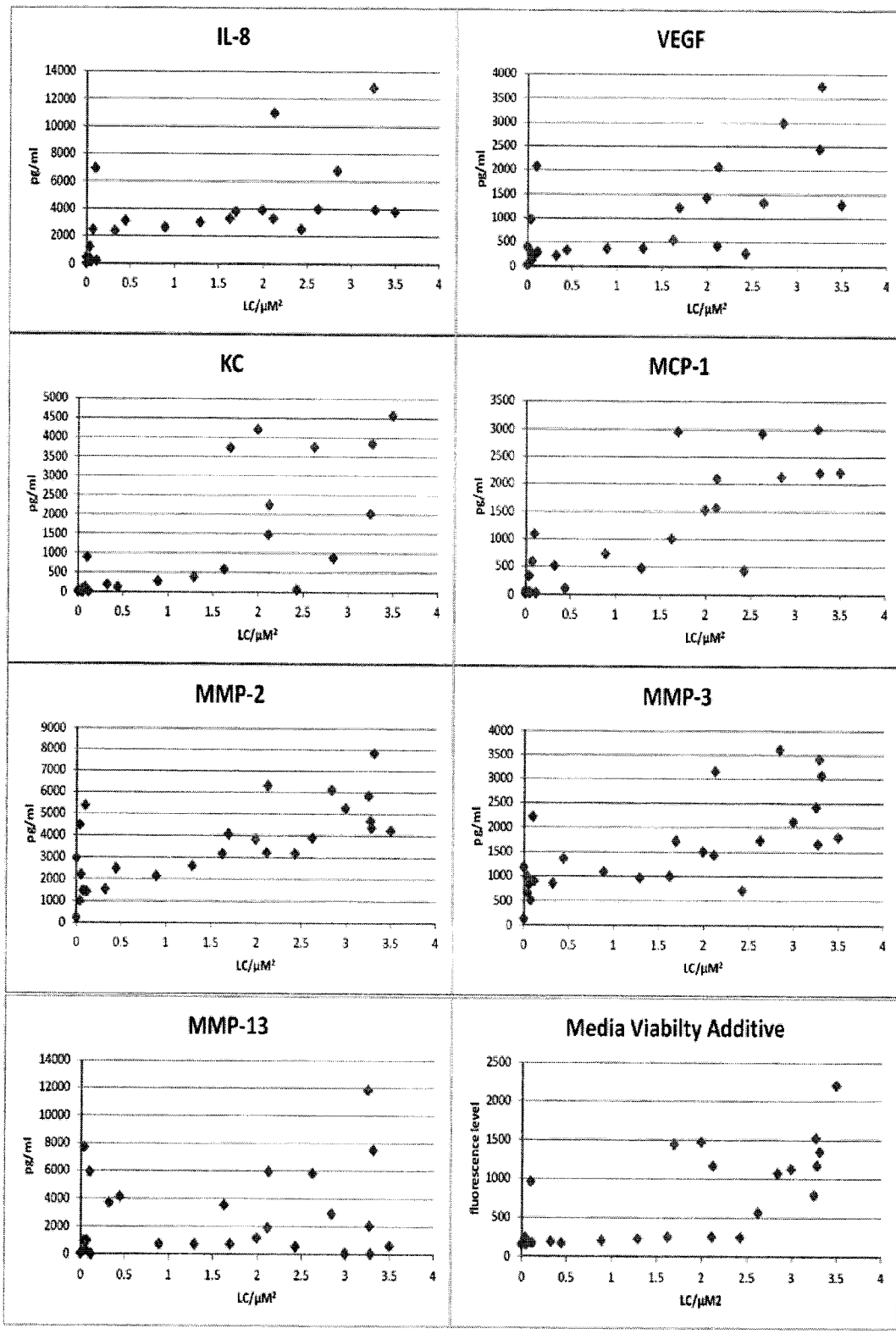
FIG. 13 shows scatter plots for each media protein biomarker (pg/ml) and the media viability additive (fluorescence level) compared to tissue viability (LC/μm2) at the end of storage (day 63-75).

Correlation Analysis (FIG. 13):

A significantly ($p<0.001$) moderate to strong positive correlation to tissue viability was found for the media viability additive ($r=0.724$), IL-8 ($r=0.598$), VEGF ($r=0.655$), KC ($r=0.738$), MCP-1 ($r=0.822$), MMP-2 ($r=0.699$), and MMP-3 ($r=0.682$). There was not a significant correlation to tissue viability for IL-6 ($r=0.385$, $p=0.0694$) and MMP-13 ($r=0.203$, $p<0.319$).

Discussion

These data indicate that similar to OCAs stored at 37 C, the concentration of proteins in the preservation media at 25° C. have the potential to act as biomarkers for identifying OCAs that have very low cell viability and therefore are not considered suitable for clinical use.

What is claimed is:

1. A process for osteochondral tissue preservation comprising storing the osteochondral tissue at room temperature in a container comprising serum-free culture medium comprising dexamethasone for from at least 63 to 75 days prior to implantation, wherein at least 70% of the cells of said osteochondral tissue remain viable after said storing compared to the viability of the cells of the osteochondral tissue at day 0.

2. The process of claim 1, comprising testing the tissue for viability at least once prior to implantation in a patient.

3. The process of claim 2, wherein testing for viability comprises assaying the medium withdrawn from said container.

4. The process of claim 2, wherein testing for viability comprises adding a resazurin solution to the medium and determining the fluorescence level, wherein increased fluorescence indicates higher cell viability.

5. The process of claim 1 comprising changing said medium at least once during the storing.

6. The process of claim 5, comprising changing the medium about once every two weeks during the storing.

7. The process of claim 1, wherein the medium comprises Dulbecco's Modified Eagle Medium (DMEM), high or low concentrations of glucose, antibiotic compounds, antimycotic compounds, ascorbate 2-phosphate, L-proline, sodium pyruvate, Transforming growth factor-β3 (TGF-β3), insulin, transferrin, and selenous acid.

8. The process of claim 1, wherein the osteochondral tissue comprises an allograft, the process comprising storing the osteochondral tissue in a tissue preservation chamber comprising a base, lid, media inlet, and media outlet; wherein the media inlet is coupled to at least a first filter for maintaining a sterile environment inside the chamber; wherein the base is configured to contain the osteochondral tissue and media; the outlet extending into the chamber to permit removal of media; the media outlet comprising a one-way valve for exit of media from the chamber; wherein the base is capable of receiving the lid to form a barrier to contaminants.

9. The process of claim 8, wherein the chamber comprises a gas exchange port coupled to at least the first filter.

10. The process of claim 9, wherein the media inlet, media outlet and gas exchange port are comprised within the lid.

11. The process of claim 1, wherein the osteochondral tissue comprises a section of spine, scapula, humerus, radius, ulna, pelvis, femur, tibia, patella, talus, phalanges or temporomandibular joint tissue.

12. The process of claim 1, wherein the osteochondral tissue comprises an allograft, the process further comprising lavaging of the osteochondral tissue in isotonic solution prior to said storing.

13. The process of claim 1, further comprising implanting the tissue in a subject in need thereof following said storing.

14. The process of claim 1, wherein the room temperature is between about 19° C. and 27° C.

15. The process of claim 1, wherein the room temperature is about 19° C., 20° C., 21° C., 22° C., 23° C., 24° C., 25° C., 26° C., or about 26° C.

16. A method for preserving osteochondral tissue at room temperature in a chamber comprising a serum-free culture medium comprising dexamethasone prior to implantation, the method comprising: placing the osteochondral tissue in a chamber base with said medium, the chamber base configured to maintain the tissue and the serum-free culture medium comprising dexamethasone; forming a tissue preservation chamber by covering the chamber base with a lid to form a barrier to contaminants, the chamber comprising at least one filter, a media inlet coupled to at least one filter for maintaining a sterile environment inside the chamber, and a media outlet, the media outlet including a media outlet conduit that extends into the chamber to permit removal of medium; wherein the media outlet comprises a one-way valve to prevent reentry of medium exiting the chamber; and storing the osteochondral tissue at room temperature for at least 63 to 75 days prior to implantation, wherein at least 70% of the cells of said osteochondral tissue remain viable after said storing compared to the viability of the cells of the osteochondral tissue at day 0.

17. The method of claim 16, wherein the chamber further comprises a gas exchange port coupled to the filter.

18. The method of claim 17, wherein the lid comprises the media inlet, media outlet, and gas exchange port.

19. The method of claim 16, further comprising adding the medium to the chamber by forcing through the media inlet and at least one filter.

20. The method of claim 16, further comprising removing the medium from the chamber through the media outlet.

21. The method of claim 16, further comprising simultaneously adding the medium to the chamber by forcing through the media inlet and at least one filter and removing the medium from the chamber through the media outlet.

22. The method of claim 16, further comprising applying tamper evident tape to an interface between the chamber base and the lid.

* * * * *